United States Patent [19]

McVey et al.

[11] Patent Number: 4,704,160
[45] Date of Patent: Nov. 3, 1987

[54] COMBINATION FERTILIZER COMPOSITION

[75] Inventors: George R. McVey; Kenneth W. Tornberg; Larry R. Widell; George E. Wood, all of Marysville, Ohio

[73] Assignee: The O. M. Scott & Sons Company, Marysville, Ohio

[21] Appl. No.: 596,006

[22] Filed: Apr. 2, 1984

[51] Int. Cl.$^4$ .................. A01N 43/64; A01N 43/60
[52] U.S. Cl. ........................................ 71/92; 71/76
[58] Field of Search ............................ 71/76, 92

[56] References Cited

U.S. PATENT DOCUMENTS

| | | | |
|---|---|---|---|
| 3,462,257 | 8/1969 | McVey et al. | 71/76 |
| 4,002,628 | 1/1977 | Benefiel et al. | 260/251 |
| 4,013,444 | 3/1977 | Fridinger | 71/76 |
| 4,243,405 | 1/1981 | Balasubramanyan | 71/76 |

OTHER PUBLICATIONS

Watschke, Agronomy Abstracts, 1982, p. 146.
Watschke, NEWSS, vol. 35, 1981, pp. 322-329.
Jagschitz, NEWSS, vol. 36, 1982, pp. 334-335.
Bingham et al., Plant Protection Results, VPI 1981, pp. 49-54.
Shearman, Univ. of Nebraska Project PG R-N82-1, 1982.
Sawyer et al., NEWSS, vol. 37, 1983, pp. 372-375.
Jagschitz et al., NEWSS, vol. 37, 1983, pp. 58-64.
Shearing et al., Joint SCI/BPGRG Monograph, 4, 1979, pp. 87-97.

Primary Examiner—Catherine L. Mills

[57] ABSTRACT

Nitrogen containing fertilizers are combined with a plant growth regulator, of the type which retards gibberellin synthesis in plants, in a ratio of nitrogen to plant growth regulator of at least 40 to one. The resulting combination fertilizer composition, when applied to vegetation at the rate of 0.006 to 0.6 pounds per acre of plant growth regulator, delivers nutrients to plants in a fashion that more closely approximates their needs than any previously known plant nutrient compositions. Preferred plant growth regulators which operate by retarding gibberellin synthesis are paclobutrazol and flurprimidol which may be used as the only plant growth regulator in the combination fertilizer composition or together with a very small amount of a second plant growth regulator, such as mefluidide.

31 Claims, 15 Drawing Figures

COMBINATION FERTILIZER COMPOSITION

BACKGROUND OF THE INVENTION

This invention relates to a combination fertilizer composition and to a process for treating vegetation with the fertilizer composition which enhances the effect of the fertilizer, extends its period of desirable response and reduces the amount of fertilizer necessary to maintain quality vegetation.

Ideal maintenance of high quality turf results when nitrogen fertilizer applications roughly coincide with the plant's nutrient demand. This balance of nutrient input and outgo has never been achieved with either quick release soluble fertilizers or with more slowly released coated or less soluble fertilizers.

Following the application of soluble fertilizers, the plant is provided an excess amount of nutrients. This is evidenced as surge growth which leads to greater labor in the culture of turfgrasses in the form of more frequent mowing and greater clipping removal. Because the plant cannot accommodate all the nutrient provided in soluble formulations, nutrients are prone to be lost to the environment via surface runoff and/or leaching. Because soluble fertilizers are not efficiently used, such products must be applied frequently and at fairly high application rates (43.6–78.4 lbs. nitrogen per acre, four to five times/year).

Slow release nitrogen fertilizers have been developed to better match nutrient availability with demand by the plant. Although certain of these slow-release nitrogen sources do provide extended residual activity, problems still remain. Certain sources (ureaform, isobutylidene diurea) are slow in providing initial greening. This encourages repeat application by the impatient homeowner. Further, these sources may not readily break down so that large quantities of nitrogen accumulate in the soil. Some slow release sources (sulfur coated urea) tend to be inefficient in that up to 30% of the nitrogen is released so slowly so as to be nutritionally insignificant. Thus, the commonly used slow release fertilizers do not optimally match plant nutrient need with availability. This results in the need for high application rates (87 to 130 lbs. nitrogen per acre, two to three times per year).

With enhanced awareness of limited fertilizer supply, high cost and potential loss of nutrients to the environment, many homeowners as well as professional turfgrass managers are reducing fertilizer application, often at the sacrifice of turf quality. There are a number of adverse effects of inadequate fertilization. Grass stands thin which promotes runoff of nutrients and soil and the stands become vulnerable to invasion by weeds which must be controlled with pesticides. Further, the aesthetic benefit of well maintained turfgrass is of course lost.

Compounds which accelerate or retard the rate of growth of plants have been known for some time. Chemicals which retard or inhibit shoot and leaf elongation can be categorized by four modes of action: (1) inhibition of mitosis in the meristematic tissue which stops cell division and cell elongation (mitotic inhibitors), (2) reduction of cell elongation by inhibiting or retarding gibberellin synthesis, a plant hormone necessary for cell elongation (gibberellin synthesis inhibitors), (3) regulating auxin activity and transport (auxin modifiers) and (4) killing terminal buds thus reducing apical dominance (chemical bud pinchers). All four modes of action are effective in higher plants; however the latter two are only moderately effective or totally ineffective on turfgrasses. Mitotic inhibitors include such compounds as chlorflurenol, mefluidide, and maleic hydrazide. Until very recently these were the only three growth regulators commercially available for use on turfgrasses. These compounds and their use as growth regulators are further discussed in "Plant Growth Regulating Chemicals", Louis G. Nickell, CRC Press, Vol. II (1983). Those which retard gibberellin synthesis include such compounds as paclobutrazol (PP-333) and flurprimidol (EL-500), discussed further below.

The combination of a plant growth regulator of the type which inhibits mitosis and a fertilizer was first reported in 1969 in McVey et al U.S. Pat. No. 3,462,257. The stated purpose of the combination was to improve turf color and quality while reducing turf growth. However, the combination product disclosed in the McVey et al patent possesses a number of limitations which have effectively prevented its use. The plant growth regulator disclosed in the McVey et al patent, 6 azauracil and certain of its derivatives and salts, requires a usage level well above the level of tolerance of certain grass species. Moreover, recovery from inhibition with this combination product is rapid, resulting in surge growth and narrower blade widths, both undesirable in turf maintenance programs.

The compounds paclobutrazol [(2RS, 3RS)-1-(4chlorophenyl)-4, 4-dimethyl-2-(1,2,4-triazol-1-yl-)pentan-3-ol] and flurprimidol [α-(1-methylethyl)-α[4-(trifluoromethoxy)phenyl]-5-pyrimidine-methanol] have been reported relatively recently as plant growth regulators. Paclobutrazol and its use as a fungicide and plant growth regulator are disclosed in U.S. Pat. No. 4,243,405 which issued on Jan. 6, 1981. The patent discloses a broad range of rates of usage for the compounds as fungicides and plant growth regulators, of from 0.1 to 15 kg per hectare (0.089 to 13.38 pounds per acre), although it indicates that applications within this range may produce phytotoxic effects on certain plants. Its use as a plant growth regulator on a variety of plants including Lolium ryegrass is shown at 5000 parts per million which, based on a conservative calculation of 80 to 200 gallons per acre of water, resulted in about 2 to 9 pounds per acre of the growth regulating compound. The patent also states that at least 75% by weight of the final fertilizer granules can be fertilizer, and up to 25% can be growth regulating compound. Flurprimidol and its use as a herbicide, fungicide and plant growth regulator are disclosed in U.S. Pat. No. 4,002,628 which issued on Jan. 11, 1977. The patent discloses that internodal elongation of plants, including turf, is inhibited by treatment with the compounds there disclosed at rates of about 0.125 to about 5 pounds per acre.

Watschke (Agronomy Abstracts, 1982 page 146) discloses the application of nitrogen fertilizer to turf 7 weeks after treating with PP-333 and EL-500. Fertilizer was applied to overcome the injury associated with these growth regulators. The article reports an improvement in turf color following application of the fertilizer, but an associated reduction in the duration of chemical suppression.

Mefluidide (N-[2,4-dimethyl-5-[[(trifluoromethyl)sulfonyl]amino]-phenyl]acetamide) is a growth regulator which inhibits mitosis (cell division) and is recommended at 0.25 to 1.0 pound in 15 to 150 gallons of water per acre. Mefluidide's use as inhibitors for the growth of grass is the subject of U.S. Pat. No. 4,013,444 to Fridinger which shows a range of suggested uses as a growth regulator of from 0.15 to 2 pounds per acre. Mefluidide has been used alone or in combination with PP-333 by a number of researchers. Rates range from 0.125 up to 0.375 pounds per acre of mefluidide when used alone (Watschke NEWSS, Vol. 35, 1981, pages 322-329, Jagschitz NEWSS, Vol. 36, 1982, pages 334-335 and Bingham et al, Plant Protection Results, VPI 1981, pages 49-54). In combination with PP-333 (0.25-2.0 pounds per acre) mefluidide has been evaluated at 0.032 up to 0.250 pounds per acre (Shearman, University of Nebraska Project PGR-N82-1, 1982, Sawyer et al NEWSS, Vol. 37, 1983, pages 372-375 and Jagschitz et al NEWSS, Vol. 37, 1983, pages 58-64 and Bingham et al, Plant Protection Results, VPI 1981 pages 49-54). The addition of mefluidide at the above rates in combination with PP-333 (0.25-2.0 pounds per acre level) had little or no effect on enhancing PP-333 activity. In contrast, Jagschitz et al NEWSS, Vol. 37, 1983, pages 58-64, used mefluidide (0.08 up to 0.125 pounds per acre) in combination with PP-333 (0.25 up to 1.00 pounds per acre) and found that growth inhibition was enhanced by the addition of mefluidide regardless of PP-333 rate. However, the turf color was considered objectionable in the presence of all rates of mefluidide during the first 4 weeks following treatment. Bingham et al, Plant Protection Results, VPI 1981, pages 49-54 reported that single applications of 0.125 to 0.375 pounds per acre of mefluidide causes discoloration of bluegrass and Kentucky 31 fescue. In combination with PP-333, rates of 0.062 to 0.25 of mefluidide with 0.25 to 2.0 pounds of PP-333 per acre also caused varying degrees of discoloration. In addition, growth of Kentucky bluegrass with the combination of growth regulators was completely stopped for 4-6 weeks.

SUMMARY OF THE INVENTION

It has now been discovered, that certain plant growth regulators of the type which retard gibberellin synthesis exhibit a unique type of biochemical synergism when combined in very small proportions with nitrogen containing fertilizers and that the use in combination with fertilizers of such compounds will both reduce surge growth and deliver nutrients to plants in a fashion that more closely approximates their needs than any previously known nutrient compositions. The plant growth regulators are used at levels below those disclosed in the literature for inhibition of growth, in most cases substantially below those levels. In the case of turf, the result is that color, quality and density are improved for a more extended period than has heretofore been possible, that less total nutrients per year are required to maintain quality turf, that growth is much more uniform and surge growth is avoided.

More specifically, the invention involves a composition for treating vegetation, and a process for its application, comprising a nitrogen containing fertilizer in combination with from 0.006 to 0.6 pounds of a plant growth regulator, said amount being based on an amount of the composition for treating one acre of vegetation, the plant growth regulator being a compound which regulates the rate of growth of vegetation by retardation of gibberellin synthesis, the ratio by weight of nitrogen in the fertilizer to the plant growth regulator being at least forty to one, the fertilizer and plant growth regulator being present in the composition in a proportion which is effective when applied to turf to improve the quality of the vegetation, the improvement in quality being both greater and extending for a longer period than that resulting from the application of fertilizer or plant regulator alone.

It has further been discovered that mixtures of a plant growth regulator which retards gibberellin synthesis and a mitotic inhibitor reduce even further the level of gibberellin synthesis retardant required to obtain the desired response. Mixtures containing a second plant growth regulator which inhibits growth by interference with mitosis, such as mefluidide or an inhibitor known as AC 252,925 [isopropylamine salt of 2-(4-isopropyl-4-methyl-5-oxo-2-imidazolin-2-yl)nicotinic acid] at extremely low rates, preferably 0.005 to 0.05 pounds per acre, reduce the initial growth rate and enhance plant quality and density even above that obtained from the combination of fertilizer and gibberellin synthesis inhibitor.

The invention is effective with both fast and slow release fertilizers but is particularly effective with slow or controlled release fertilizers, such as those prepared from the condensation of urea and formaldehyde, e.g. methylene urea, or by coating a soluble nitrogen source, e.g. sulfur coated urea. A typical fast release fertilizer is urea. The most effective turf growth regulators have been found to be paclobutrazol and flurprimidol, both more specifically identified above, and these are accordingly the preferred growth regulators of the invention. The invention is especially adapted for the treatment of turf but has also been found to be effective with other vegetation, e.g. vegetable and ornamental plants.

All of these advantages are not obtained or obtainable with the fertilizer or plant growth regulator alone. For purposes of clarity, the advantages are discussed herein in connection with turf, for which the present invention is particularly adapted. However, it should be understood that the invention and its advantages are applicable to a variety of vegetation and the invention is not intended to be limited except as set forth in the claims.

The invention makes possible not only the production of a higher quality turf but a higher quality turf for a longer period of time than that obtainable by using either the same plant growth regulator or the same fertilizer alone. By the use of a typical combined slow release fertilizer and plant growth regulator of the invention, the peak nutrient uptake period is shifted from 2 to 3 weeks to 6 to 8 weeks after fertilization. This results in a reduction of surge growth which occurs after fertilization and an extension of turf color and quality 2 to 4 weeks, in some instances considerably more than 2 to 4 weeks, beyond that achieved with the fertilizer alone. In addition, the color of the turf is improved both initially and after the growth rate has returned to normal. Moreover, the amount of fertilizer required to maintain good turf color and quality is reduced over the amount required without the growth regulator.

The fertilizers, when used in the proportions herein set forth, tend to act as antidotes for the otherwise injurious action of the plant growth regulator on turf or other plants. Furthermore, the nitrogen/plant growth regulator ratios herein set forth provide biological activity an extremely low rates of the plant growth regulator as a result of synergism between these two components. Moreover, by using small proportions of the growth regulator, either simultaneously with or while the turf is actively growing as a result of the application of the nitrogen fertilizer, injury to the vegetation is eliminated. The fertilizer should be applied simultaneously with application of the regulator, and in any event, before the growth regulator damages the turf. Reference herein to application of the fertilizer and growth regulator in combination is intended to encompass the application of the materials in either of these fashions, that is either simultaneously which is preferable, or within a relative short period of time after the application of the fertilizer or the growth regulator. The time period will vary with the type and amount of fertilizer and growth regulator but should normally be no longer than a week.

It has been found that there is less criticality in the method and rate of application of the combined fertilizer and growth regulator than there is with the growth regulator alone. That is, the invention makes possible a wide margin of safety between desirable turfgrass response and objectionable phytotoxicity. Moreover, repeat applications may be carried out without danger of an adverse effect on the turf. Most known plant growth regulators, particularly mitotic inhibitors, are in fact herbicides at higher application rates and when used even at low application rates have a phytotoxic potential. The invention involves using only those plant growth regulators (alone or in combination with a mitotic inhibitor) which operate by retardation of gibberellin synthesis and only at extremely low rates, sufficient to obtain biological response and yet have an adequate margin of safety. The invention also involves using very high proportions of nitrogen to mitigate any phytotoxic effect, even at multiples of normal nitrogen application rates. The advantages of the invention are particularly unexpected in view of the previous sensitivity of turf to the level of application of plant growth regulators. In addition, the invention has been found to be effective on a broad variety of turf species and over a wide geographical area.

The term "plant growth regulator" as used herein means a substance intended, through physiological action, to retard the rate of growth or rate of maturation, or otherwise alter the behavior of plants. A more complete discussion of plant growth regulators is contained in the aforesaid text "Plant Growth Regulating Chemicals", by Louis G. Nickell. Those growth regulators included within the scope of the invention whose mode of action affects gibberellin synthesis are defined in the literature as inhibitors of gibberellin synthesis. However, the growth regulating compounds are used in the present invention in formulations and at rates which retard rather than stop or suppress the growth of vegetation. Accordingly, the compounds which affect gibberellin synthesis are referred to herein as those which retard gibberellin synthesis.

DESCRIPTION OF THE PREFERRED EMBODIMENTS

Figure 1:
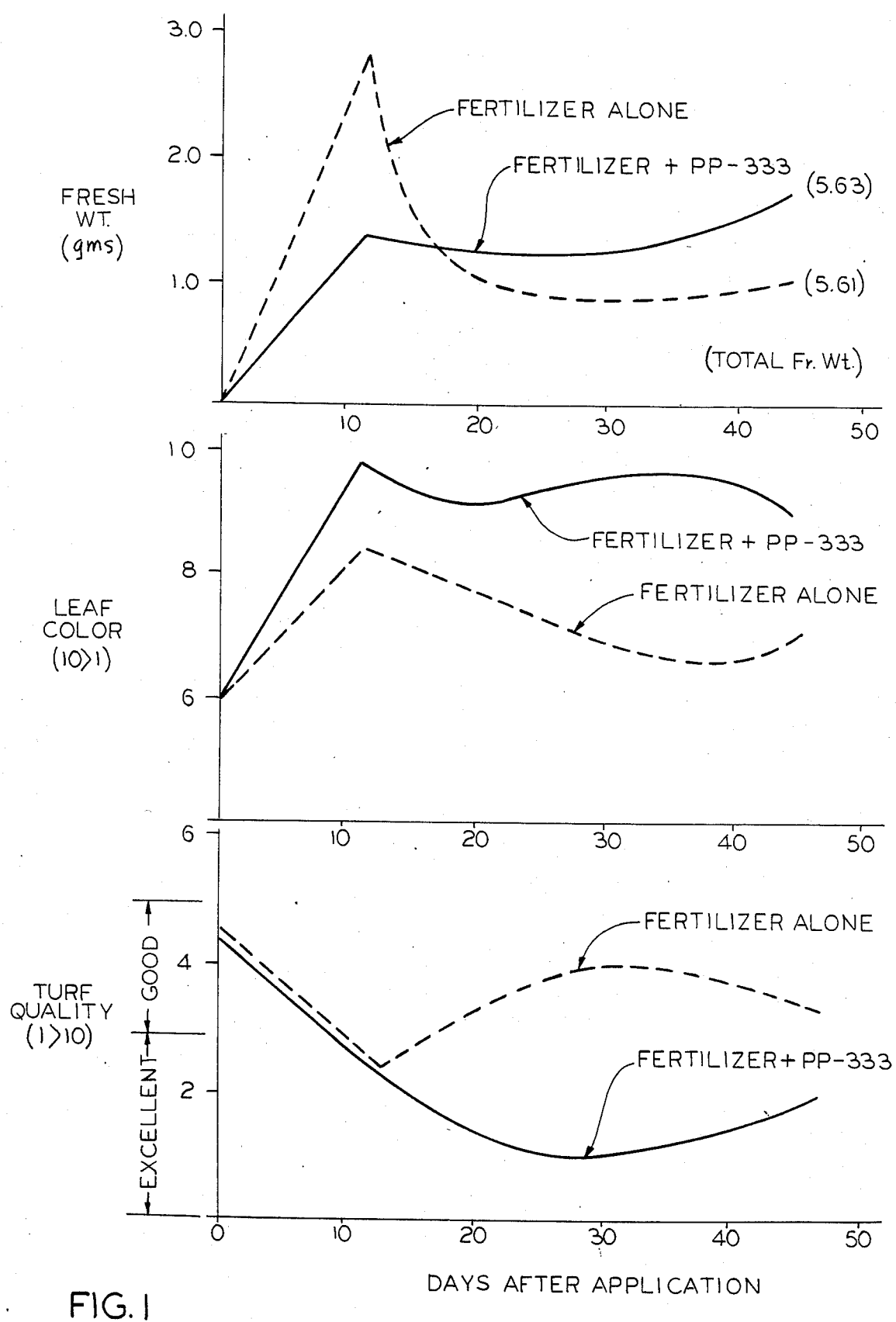
FIG. 1 is a graph comparing, in three different respects, turf treated with the combined fertilizer plant growth regulator compositions of the invention with turf treated with the fertilizer alone.

In the practice of the invention, specific ranges of plant growth regulators are required. The gibberellin synthesis retardants-plant nutrient combination should be applied at rates providing from 0.006 to 0.6 pounds per acre of the gibberellin synthesis retardant. With most turfgrasses, this amount preferably varies from 0.05 to 0.5 pounds per acre. At these rates, in the absence of fertilizer, the plant growth regulators have only a very slight effect on turf performance. In some cases, there is a slight improvement in turf quality while in other cases, there is deterioration. The addition of fertilizer both stimulates growth and at higher rates partially overrides the retarding effect of these chemicals. However, by selecting the proper balance of nutrient to growth regulator, the growth can be controlled. The plant nutrient should contain nitrogen in an amount at least forty times greater than the amount of the gibberellin synthesis retardant on a weight to weight basis. At ratios below forty, there is a probability of inhibition of plant growth. Optimum ratios of nitrogen to plant growth regulator for cool season grasses should range from 60 to 600 and for warm season grasses from 40 to 300. The amount of fertilizer will normally vary from 20 to 180 pounds of nitrogen per acre from either an organic or inorganic source, the specific amount depending on the type of fertilizer used. Less than 20 pounds of nitrogen per acre produces inadequate results. More than 180 pounds per acre tends to override the effect of the plant growth regulator. With methylene urea type fertilizers, this amount will normally vary from 20 to 90 pounds of nitrogen per acre; with sulfur coated urea, the amount will normally vary from 40-180 pounds of nitrogen per acre. The active ingredients may be applied as a foliar spray or combined with a solid carrier and spread on the area to be treated, and the active ingredients may be combined in a single formulation or applied separately, either at the same or at different times. The duration of the benefits derived from the fertilizer/plant growth regulator combination ranges from 8 to 12 weeks or longer, depending upon the rate of application of the active ingredients and whether they are applied separately or in a single formulation.

The following examples illustrate the practice of the invention. Unless otherwise indicated, all parts and percentages are by weight. Also, unless otherwise indicated, reference in the examples to application rates indicates pounds of nitrogen, in the case of fertilizers, and pounds of active ingredient, in the case of plant growth regulators, applied to one acre of vegetation. The various measurements and tests carried out on turf were conducted as follows:

Leaf Color: The intensity of green was estimated using a scale of 10 to 1 with 10 being a very excellent dark green color. Acceptable turf color ranges from 7-10. For excessively dark green turf which may appear unnatural, values of 11–15 are used with 15 being a very dark gray-green color.

Leaf or Turf Quality: Turf quality was rated on a scale of 1 to 10 with 1 being a very excellent quality. Quality was based on color, uniformity of growth, density and texture (uniformity of blade width). A rating of 1–3 is considered excellent with acceptable quality ranging up to 6.

Height: The turf was measured from the mowing height to the average height of the new growth in greenhouse tests. Under field conditions the height was taken from the soil surface to the average height of the new blades.

Leaf Fresh Weight: Under greenhouse conditions, turf was grown in pots and cut at pot level. Since the soil level was 1.5 inches below the rim of the pot, the turf was cut at a 1.5 inches mowing height. These clippings were weighed immediately after clipping. Under field conditions, turf was cut with a gas powered lawn mower. The clippings were blown into plastic bags which were tied and immediately weighed.

Blade Width: The widest part of the blade was measured (2–4 cm from the tip of the blade.)

Density: Determined by a double cut method. The turf was cut at 3 inches, then recut at 2.5 inches. The clippings collected at the 2.5–3.0 inch zone were weighed to determine leaf blade density.

EXAMPLE 1

A combination growth regulator-fertilizer product for use in accordance with the invention was prepared on a common carrier from the following constituents:

|  | Percent |
| --- | --- |
| Fertilizer[1] | 81.84 |
| Hexylene glycol | 9.46 |
| Solvent (M-Pyrol)[2] | 2.16 |
| Surfactant (T-Det N-9.5)[3] | 2.16 |
| Dust (Hi Sil 233)[4] | 4.31 |
| PP-333, 95%[5] | .07 (0.066) |

[1]The fertilizer was a high nitrogen fertilizer having a 27-3-3 analysis of N, P$_2$O$_5$ and K$_2$O derived from urea, methylene ureas, monammonium phosphate and potassium chloride with 66% of N in a slow release methylene urea form.
[2]M-Pyrol is a brand name for N—methyl-2-pyrrolidone.
[3]T-Det N-9.5 is a brand name for an adduct of nonylphenol and 9.5 moles of ethylene oxide.
[4]Hi Sil 233 is a brand name for a fine powder precipitated hydrated silica.
[5]The 95% technical grade PP-333 was .07% of the formulation amounting to 0.066% PP-333 active ingredient.

The technical grade PP-333 was dissolved in the solvent and surfactant. This solution was sprayed onto the Hi Sil dust. The dust containing the active solution was fed into a blender containing the fertilizer. Hexylene glycol solution was sprayed onto the fertilizer dust mixture to adhere the active dust to the fertilizer particles.

EXAMPLE 2

In order to conduct comparative tests with the composition of Example 1, a formulation was prepared containing the growth regulator alone. This formulation was prepared from the following constituents:

|  | Percent |
| --- | --- |
| Vermiculite | 78.31 |
| Hexylene glycol | 13.37 |
| Solvent (M-Pyrol) | 2.06 |
| Surfactant (T-Det N-9.5) | 2.06 |
| Dust (Hi Sil 233) | 4.13 |

-continued

|  | Percent |
| --- | --- |
| PP-333 (95%) | 0.07 (0.0665) |

The technical grade PP-333 was dissolved in the solvent plus the surfactant. This solution was sprayed onto the Hi Sil 233 dust. The dust containing the active solution was fed into a blender containing the vermiculite carrier. Hexylene glycol solution was sprayed onto the vermiculite dust mixture to adhere the active dust to the vermiculite particles.

In order to determine the general biological activity of this composition, plots of Bristol Kentucky bluegrass were then treated with (1) the high analysis 27-3-3 fertilizer used in the formulation of Example 1 but without the growth regulator, (2) the plant growth regulator formulation of Example 2, (3) separate but simultaneous applications of both the fertilizer and the Example 2 growth regulator formulation and (4) the combination product of Example 1. The various formulations were applied to dry foliage and watered in with 0.25 inches of water. Results were obtained over a 100 day period by averaging the responses obtained on the 7th, 23rd, 31st, 53rd, 68th, and 100th day with respect to leaf color and turf quality.

TABLE I

| Sample No | Formulation | Rate (lbs/acre) N | Rate (lbs/acre) PP-333 | Leaf Color % Of Control[1] | Turf Quality % of Control |
| --- | --- | --- | --- | --- | --- |
| 1. | Fertilizer | 58.8 | 0 | 120 | 131 |
| 2. | Plant Growth Regulator | 0 | 0.18 | 131 | 102 |
| 3. | Fertilizer & PGR Separate Carriers | 58.8 | 0.18 | 186 | 159 |
| 4. | Fertilizer & PGR Common Carrier | 58.8 | 0.18 | 164 | 140 |

[1]The control received no fertilizer or PGR.

Table 1 shows that a combination of fertilizer and plant growth regulator is far more effective than either one by itself in improving leaf color and turf quality, the greatest improvement resulting from the application of the fertilizer and growth regulator on separate carriers.

EXAMPLE 3

A series of tests were conducted comparing fertilizers alone with combination fertilizer products in accordance with the invention. Bristol Kentucky bluegrass was grown in the greenhouse in sand and maintained with a complete Hoagland solution using 50 ml of a 210, 30 and 240 ppm N, P and K fertilizer. A Hoagland solution contains 210 ppm (parts per million) N, 30 ppm P, 234 ppm K, 200 ppm Ca, 48 ppm Mg, 64 ppm S, 0.5 ppm B, 0.02 ppm Cu, 5 ppm Fe, 0.5 ppm Mn, 0.01 ppm Mo and 0.05 ppm Zn as KNO$_3$, Ca(NO$_3$)$_2$.4H$_2$O, MgSO$_4$.7H$_2$O, KH$_2$PO$_4$, Sequestrene 138 (trademark for chelated iron source) ZnSO$_4$.H$_2$O, H$_3$BO$_3$, MnCl$_2$.H$_2$O, CuSO$_4$.5H$_2$O, H$_2$MoO$_4$.H$_2$O. The solution was applied weekly which equates to 43.5 pounds of N/acre per month. When the turf was fully mature (6 months), the fertilizer formulation of Example 1 alone was applied at 69.7 pounds N/acre or fertilizer was applied at this rate along with 0.06 pounds per acre of PP-333 applied as a liquid drench. The total fresh weight, color and quality of the turf was measured at intervals for 48 days after initial application of the fertilizer or fertilizer and PP-333. The results are show in FIG. 1.

As shown in FIG. 1, the total leaf fresh weight (upper graph) was not significantly reduced as a result of the treatment with the combination fertilizer PP-333 product. However, the leaf fresh weight distribution was dramatically altered as compared to turf treated with the fertilizer alone. The growth of the turf treated with the combination product was more uniform and predictable from harvest to harvest. Along with the uniform turf growth response (reduced surge growth) was an improvement in turf color and quality, as is evident from the lower two graphs.

EXAMPLE 4

A series of comparative tests were conducted in the greenhouse to compare combination fertilizer products of the invention which retard plant growth by retardation of gibberellin synthesis with products containing various well known plant growth regulators outside the scope of the invention which inhibit or retard plant growth by reduced cell division or mitosis. The known growth regulators included in the test were cycocel[(2-chloroethyl)trimethylammonium chloride], 6 azauracil, morphactin(methyl 2-chloro-9-hydroxy fluorene-9-carboxylate), mefluidide and ethrel ((2-chloroethyl)phosphonic acid). Bristol Kentucky bluegrass was grown in pure silica sand and maintained with a Hoagland solution containing all essential elements. The solution was applied weekly using 210, 30 and 240 ppm of nitrogen, P and K respectively. This is the equivalent of 43.5 pounds N/acre/month. Solutions of the growth regulators were applied as a drench at 0.02, 0.2 and 2.0 pounds per acre in 50 ml of water. Fresh weight, height, color and blade width measurements were made at the end of thirty days. For comparison, a control sample was not treated with a growth regulator. All samples were treated with 43.5 pounds N/acre. The fresh weight and height results are set forth in Table II and the color results are set forth in Table III.

TABLE II

| Sample No. | PGR | Fresh Weight (gms) lbs/acre PGR | | | | Height (cm) lbs/acre PGR | | | |
|---|---|---|---|---|---|---|---|---|---|
| | | 0 | 0.02 | 0.2 | 2.0 | 0 | 0.02 | 0.2 | 2.0 |
| 1 | Cycocel | 1.54 | 1.79 | 1.61 | 1.54 | 7.8 | 7.7 | 7.5 | 7.2 |
| 2 | 6 Azauracil | 1.54 | 1.55 | 1.69 | 0.40 | 7.8 | 7.7 | 7.7 | 4.7 |
| 3 | Morphactin | 1.54 | 1.56 | 1.55 | 1.97 | 7.8 | 8.4 | 8.0 | 8.3 |
| 4 | Mefluidide | 1.54 | 1.79 | 2.00 | .42 | 7.8 | 8.0 | 8.0 | 4.8 |
| 5 | Ethrel | 1.54 | 1.62 | 1.68 | 1.90 | 7.8 | 7.5 | 7.8 | 7.2 |
| 6 | PP-333 | 1.54 | 1.10 | 0.10 | 0 | 7.8 | 5.2 | 3.0 | 3.0 |

TABLE III

| Sample No. | PGR | Color (10 > 1) lbs/acre PGR | | | |
|---|---|---|---|---|---|
| | | 0 | 0.02 | 0.2 | 2.0 |
| 1 | Cycocel | 7.8 | 8.2 | 8.0 | 8.0 |
| 2 | 6 Azauracil | 7.8 | 8.2 | 7.4 | 10.0 |
| 3 | Morphactin | 7.8 | 8.0 | 8.0 | 8.3 |
| 4 | Mefluidide | 7.8 | 8.0 | 7.8 | 7.5 |
| 5 | Ethrel | 7.8 | 8.7 | 8.3 | 8.0 |
| 6 | PP-333 | 7.8 | 10.0 | 9.7 | 6.7 |

Tables II and III show that a product containing the gibberellin retardant PP-333 in combination with the fertilizer is more biologically active than any of the other combination products tested. Turf treated with cycocel, morphactin and ethrel exhibited little or no response to treatment in most of the results measured. Combination products containing 6 azauracil had little or no effect at 0.02 and 0.2 pounds per acre. Turf treated with the fertilizer PP-333 combination exhibited less growth in height and a greater color improvement at a lower rate than all of the other combination products. For example, 0.02 pounds of PP-333/acre in combination with fertilizer induced similar or greater turf color improvement and similar or greater reduction in height than all other growth regulators operating by mitotic inhibition applied at 100 times the rate of application (2.0 pounds per acre). The color of the turf treated with PP-333 decreased at 2 pounds per acre. This application rate is over three times the maximum application rate of the invention.

Increased blade width is generally considered a desirable characteristic of turf. Table III shows that most of the combination products tested containing a mitotic inhibitor had at most a moderate and in some cases, a negative impact on blade width. The combination product containing cycocel had a slight improvement at the 2 pounds per acre level. Morphactin, mefluidide and ethrel products all produced a slight reduction in blade width. 6 azauracil produced a dramatic reduction in blade width. The increase in blade width produced with the combination product containing the gibberellin retardant PP-333 is reflected not only in the blade width measurements but also in the improved color.

EXAMPLE 5

Figure 2:
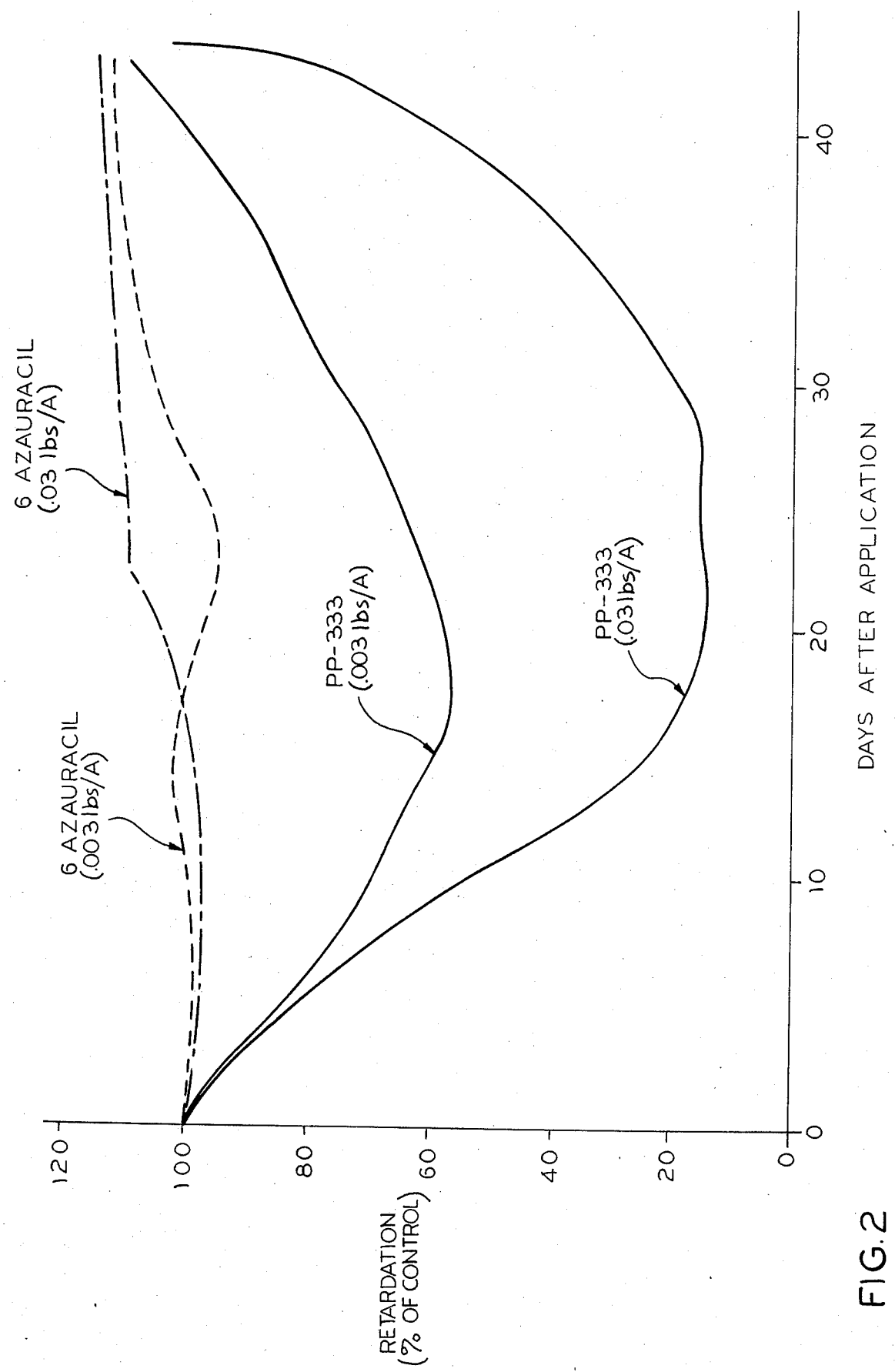
FIGS. 2-6 are graphs comparing the growth of turf treated with combination fertilizer composition of the invention with comparable combination products containing mitotic inhibitors.

A series of tests were conducted to compare the range of biological activity of PP-333 and 6 azauracil, both when combined with a fertilizer. Bristol Kentucky bluegrass was grown in silica sand and treated with 25 ml of water containing 0.1 or 1 ppm (0.003 and 0.03 pounds per acre) of the growth regulator. The turf was maintained on complete Hoagland solutions using 43.56 pounds of N/acre per month. FIG. 2 plots the percent of retardation at various intervals for 45 days, based on the fresh weight of clippings. This percent is the retardation measured relative to a plot with no growth regulator added. As shown in FIG. 2, 6 azauracil exhibited no biological activity at the rates tested, i.e. retardation was approximately the same as the control. On the other hand, PP-333 exhibited excellent activity even at the rate of 0.003 pounds per acre.

Figure 3:
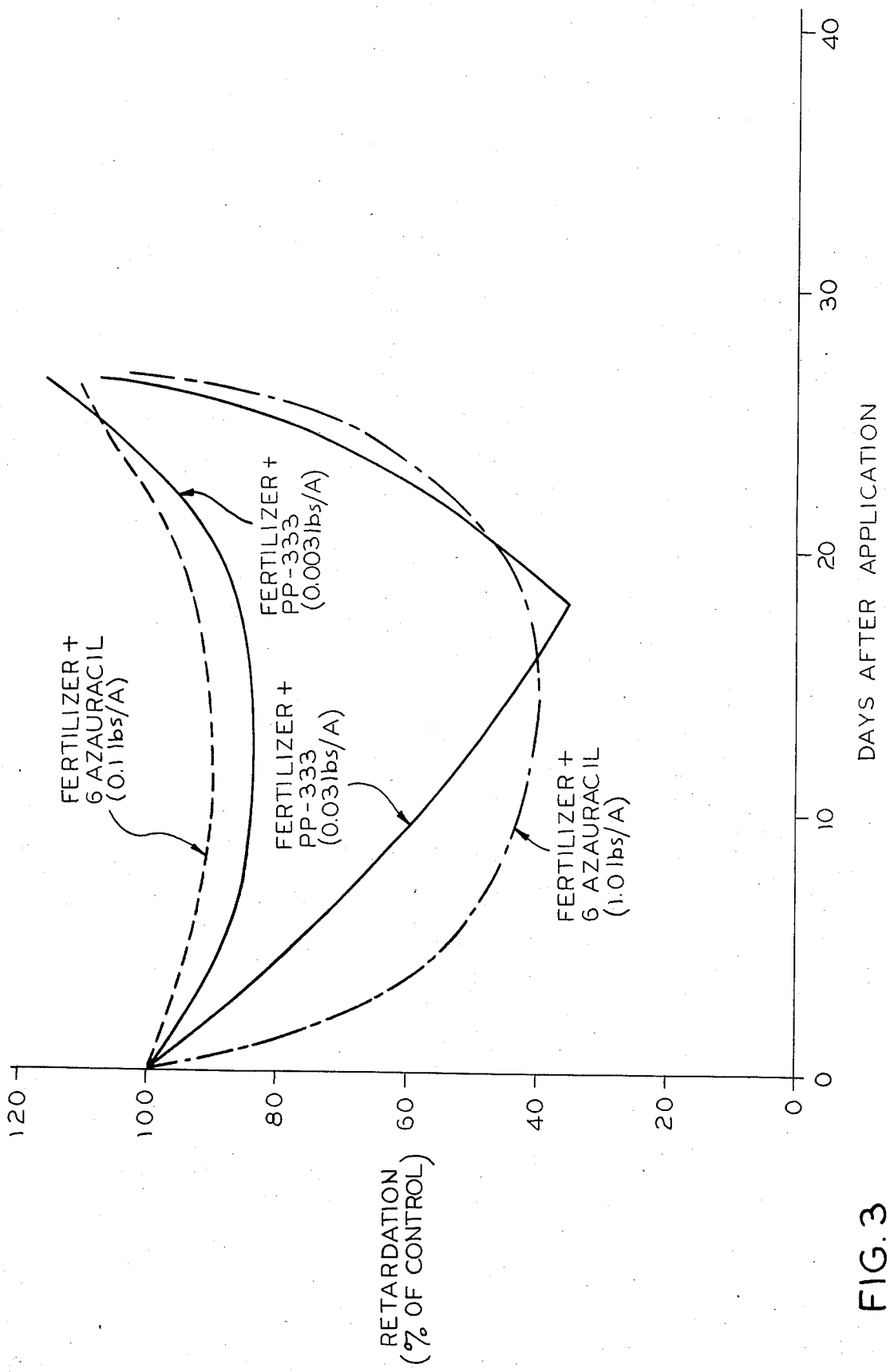

A second series of tests were made using higher rates of 6 azauracil and these are plotted in FIG. 3. As there shown, 6 azauracil exhibited no activity at 0.1 pounds per acre and substantial activity at 1.00 pounds per acre. The biological activity of PP-333 when combined with a fertilizer was thus 33 times greater than the same amount of 6 azauracil.

EXAMPLE 6

In order to further compare combination products containing fertilizers and growth regulators, a series of combination products were prepared containing gibberellin synthesis retardants, on the one hand, and 6 azauracil, on the other hand. In this example, a fertilizer—PP-333 combination product, a fertilizer—EL-500 combination product and a fertilizer—6azauracil combination product were each prepared in granular form on a common carrier from the following formulations:

|  | Percent |
|---|---|
| Fertilizer[1] | 96.01 |
| Hexylene glycol | 2.94 |
| Dust (Hi Sil 233) | 0.89 |
| PP-333 (50%) | 0.16 (0.08) |
| Fertilizer[1] | 95.94 |
| Hexylene glycol | 2.94 |
| Dust (Hi Sil 233) | 0.64 |
| EL-500 (50%) | 0.48 (0.24) |
| Fertilizer[1] | 95.60 |
| Hexylene glycol | 2.35 |
| Surfactant (Tween 20)[2] | 0.72 |
| 6-azauracil | 1.33 |

[1]The fertilizer in each formulation was the same as that used in Example 1.
[2]Tween 20 is polyoxyethylene 20 sorbitan monolaurate.

The 50% wettable powder PP-333 and EL-500 were blended with the dust. This mixture was fed into a blender containing the fertilizer. Hexylene glycol solution was sprayed onto the fertilizer/dust mixture to adhere the active dust to the fertilizer particles. The technical grade 6 azauracil was suspended in the hexylene glycol/Tween 20 solution mixture. The solution containing the active was sprayed onto the fertilizer carrier in a blender.

EXAMPLE 7

A series of greenhouse tests were carried out to compare the combination products of Example 6 with a fourth granular formulation identical to that of Example 6 but omitting the growth regulator. Bristol Kentucky bluegrass was grown in a 3/1 sand/loam soil mixture contained in 4" diameter pots (400 ml) and was treated with the foregoing formulations. The formulations were applied in granular form to dry turf and watered in immediately. As a control, a fifth sample of Bristol Kentucky bluegrass was watered but not treated with any of the formulations. All fertilizer formulations were applied at the rate of 58.8 pounds of nitrogen per acre. The PP-333 was applied at the rate of 0.18 pounds per acre and the EL-500 was applied at the rate of 0.54 pounds per acre. The 6 azauracil was applied at 3 pounds per acre. These were found to be the optimum rates of application for these growth regulators in these tests.

Figure 4:
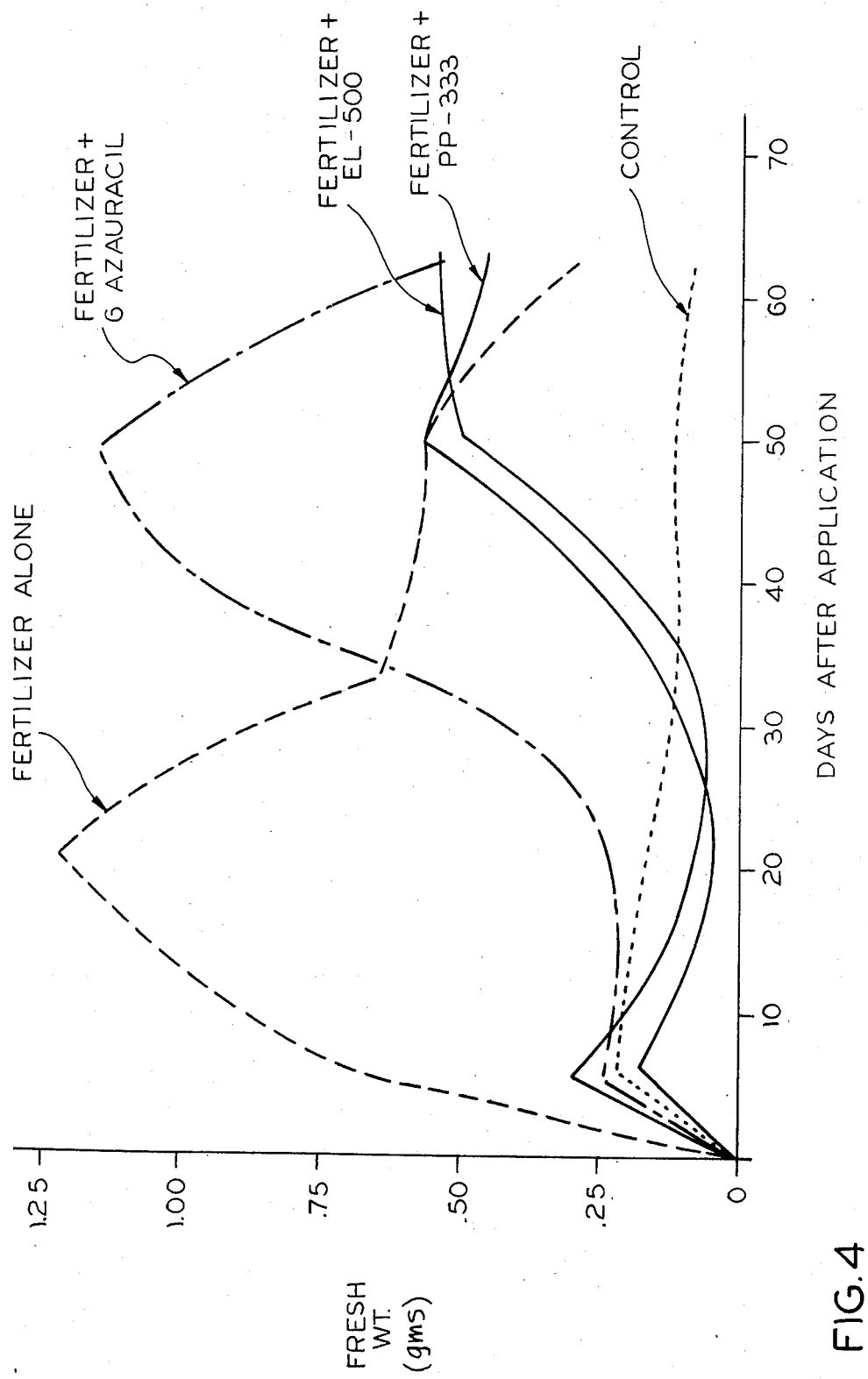

FIG. 4 shows the results of leaf fresh weights taken at various intervals during a 65 day period for the (1) fertilizer alone, (2) the fertilizer—6azauracil combination product, (3) the fertilizer—EL-500 combination product, (4) the fertilizer—PP-333 combination product and (5) a control sample with neither fertilizer nor growth regulator. As shown by FIG. 4, surge growth, as measured by fresh weight of turf, was reduced by all combination products during the first three weeks of the study. However, subsequent growth of the turf treated with fertilizer and 6 azauracil dramatically accelerated from the beginning of the third week through approximately the seventh week. The resulting surge of growth was comparable to the earlier surge of growth for turf treated with fertilizer alone. Turf treated with combination products containing PP-333 and EL-500 show gradual increase in growth from day 30 to day 65 with no surge evident. Fresh weight measurements can reflect either or both an increase in the height of the turf or an increase in its density. Height measurements of the turf tested in this example indicated that the surge growth with both 6 azauracil and the fertilizer was a result of increased height of the turf, rather than an increase in density.

Measurements were also made at various intervals of the color and quality of the turf tested in Ex. 7. The results are shown in Tables IV and V.

TABLE IV

| Sample No | Product | Color (10 > 1) Day | | | |
|---|---|---|---|---|---|
| | | 20 | 34 | 50 | 62 |
| 1 | Fert. + PP-333 | 10 | 10 | 10 | 10 |
| 2 | Fert. + EL-500 | 9.3 | 9 | 9 | 9.3 |
| 3 | Fert. + 6 azauracil | 9 | 8.3 | 7.7 | 6.0 |
| 4 | Fert. alone | 7 | 5.7 | 6.3 | 4.7 |
| 5 | Control | 1 | 1 | 1 | 2 |

TABLE V

| Sample No | Product | Quality (1 > 10) Day | | | |
|---|---|---|---|---|---|
| | | 20 | 24 | 50 | 62 |
| 1 | Fert. + PP-333 | 2.0 | 2.0 | 1.7 | 1.7 |
| 2 | Fert. + EL-500 | 3.0 | 3.0 | 2.0 | 2.0 |
| 3 | Fert. + 6 azauracil | 3.7 | 3.0 | 3.0 | 6.0 |
| 4 | Fert. alone | 2.3 | 3.7 | 4.7 | 3.7 |
| 5 | Control | 2.7 | 8.0 | 8.3 | 9.0 |

It is evident from Tables IV and V that both the color and quality of turf treated with fertilizer and PP-333 or EL-500 was excellent while the turf treated with fertilizer in combination with 6 azauracil exhibited deterioration in both color and quality following the delayed surge of growth, i.e. see the results at 62 days.

EXAMPLE 8

An additional series of greenhouse tests were carried out to compare combination products of the invention containing gibberellin retardants with similar products containing mitotic inhibitors. Four combination products were applied to five year old Bristol Kentucky bluegrass grown in a 3/1 sand/loam soil mixture contained in 4" cups (400 ml). All plant growth regulators were applied as a drench using 50 ml containing 3.12 ppm (0.1875 pounds per acre). The fertilizer was a high analysis fertilizer having a 27-3-3 analysis of N, $P_2O_5$ and $K_2O$ derived from urea, methylene ureas, monoammonium phosphate and potassium chloride with 60 percent of the nitrogen in a slow release form (methylene ureas). A control sample was fertilized but not treated with a plant growth regulator. The fertilizer was applied at 52.2 pounds of N/acre in all samples. Results were recorded on the 55th day after application. The results are set forth in Table VI.

TABLE VI

| Sample No | Inhibitor | Color 10 > 1 | Quality 1 > 10 | Height (cms) | Fresh Wt. (gms) | Ht/FW |
|---|---|---|---|---|---|---|
| 1 | PP-333 | 10 | 2 | 2.5 | 1.21 | 2.1 |
| 2 | EL-500 | 8 | 3 | 3.5 | 1.17 | 2.99 |
| 3 | Mefluidide | 5 | 5 | 4.0 | .78 | 5.1 |
| 4 | AC 252,214* | 5 | 9 | 6.0 | .48 | 12.5 |
| 5 | None (Control) | 4 | 5 | 4.1 | .80 | 5.1 |

*AC 252,214 also known by the trademark Scepter, contains the active ingredient 2-[4,5-dihydro-4-methyl-4(1-methylethyl)-5-oxo-1H—imidazol-2-yl]-3-quinolinecarboxylic acid.

As shown in Table VI, the combination products containing gibberellin synthesis retardants (samples 1 and 2) reduced turf height but increased fresh turf weight resulting in a height/fresh weight (Ht/FW)

ratio of 2-3. In contrast, the combination products containing mitotic inhibitors, samples 3-4, caused a comparable increase in turf height and reduction in fresh weight resulting in a Ht/FW of 5 to over 12. The difference in these ratios is a quantitative expression of the difference between the desirable, low compact dense turf (low ratios) and the undesirable, tall spindly turf (high ratios.)

EXAMPLE 9

Figure 5:
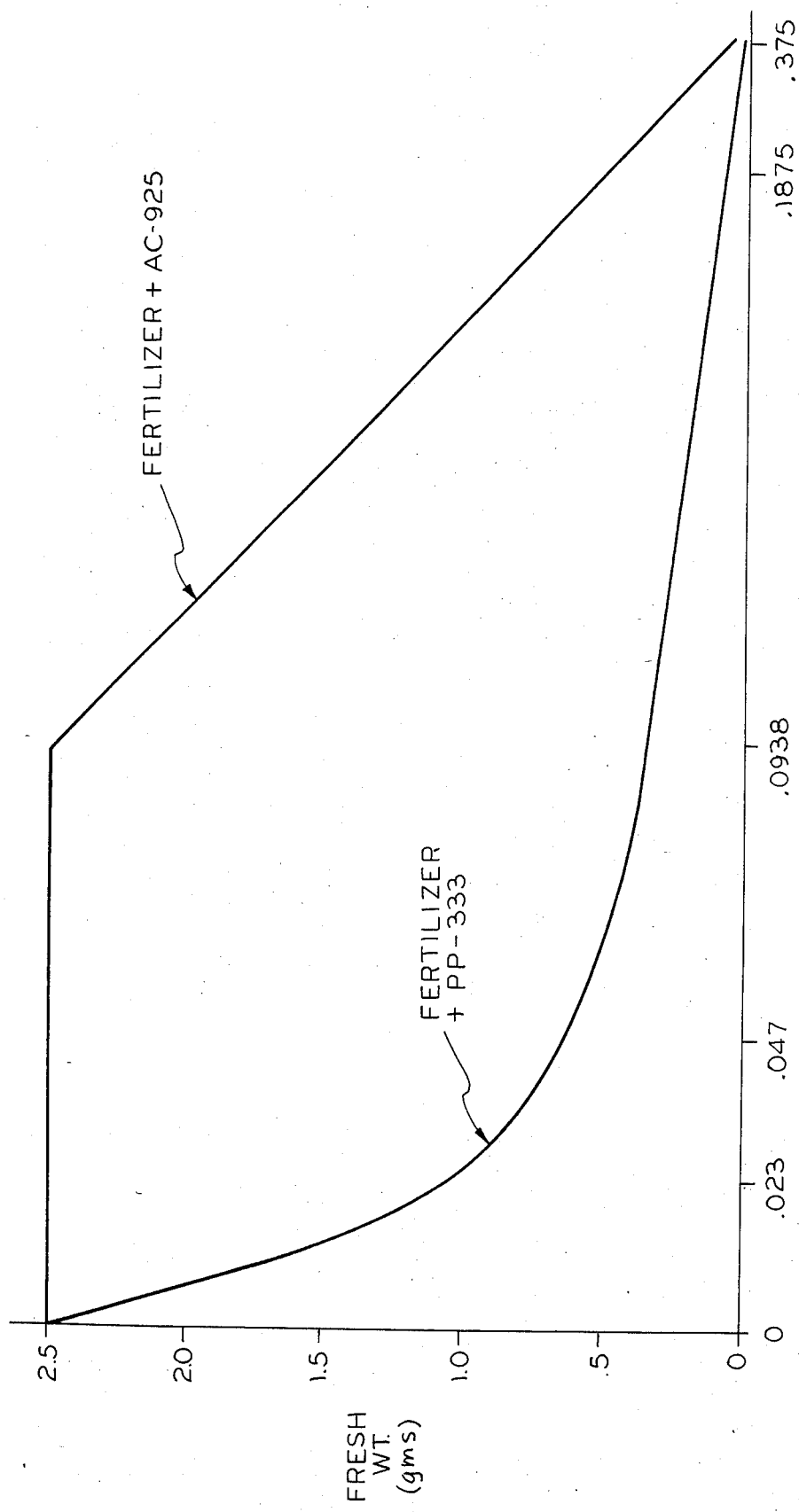

The comparative tests of Example 8 were repeated with two treatments, one a fertilizer and PP-333 and the second a fertilizer and a known mitotic inhibitor, AC 252,925 (hereafter referred to as AC 925). AC 925 is also known by the trademark Arsenal. It is further disclosed in Los, M. et al, A New Class of Herbicides, American Chemical Society Abstracts, Mar. 20-25, 1983. The growth regulators were applied as a liquid at rates varying from 0 to 0.375 pounds per acre in combination with 52.2 pounds of nitrogen per acre as described in Example 8. As shown in FIG. 5 the leaf fresh weight contrasts the responses of these two combination products. The gibberellin retardant, PP-333, has a gradual retarding effect over a broad range of from 0 to 0.375 pounds per acre with the degree of retardation depending on the rate of application. In contrast, the mitotic inhibitor, AC-925, exhibited no biological activity at rates up to 0.093 pounds per acre, then extreme activity to 0.375 pounds per acre where inhibition was almost total, suggesting an on/off switch mechanism of action. The gibberellin synthesis retardant in contrast gradually reduces rather than stops the synthesis of gibberellin as the rate increases, permitting a controlled growth response.

EXAMPLE 10

Figure 6:
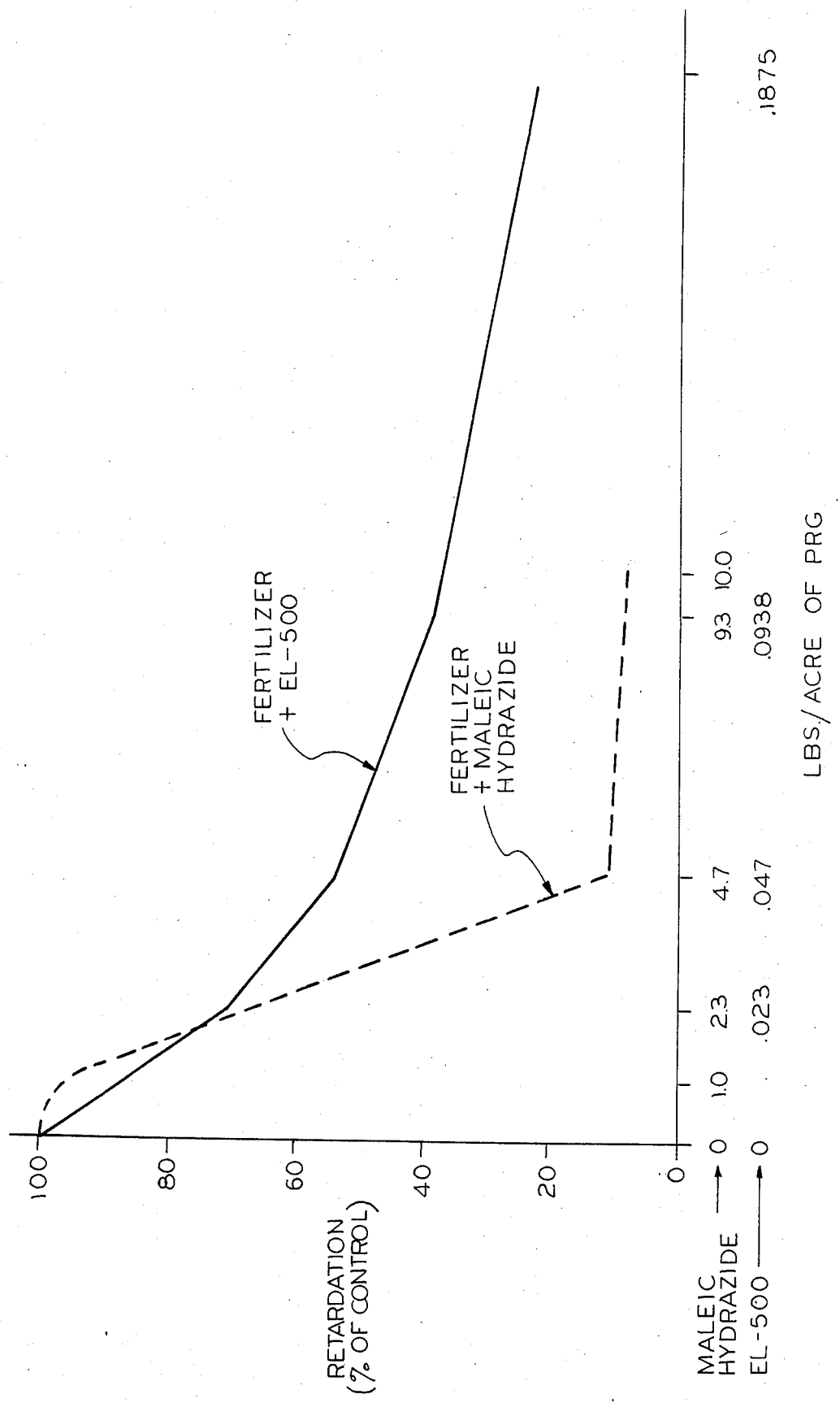

A further comparison was made between treatments containing gibberellin synthesis retardants, on the one hand, and mitotic inhibitors, on the other hand. The gibberellin synthesis retardant was EL-500. The mitotic inhibitor was maleic hydrazide (1,2-dihydro-3,6-pyridazinedione). Maleic hydrazide is one of the most widely used growth regulators in the U.S. It has been known for some time to have growth regulating properties on turfgrasses. Bristol Kentucky bluegrass plots in a 3/1 sand/loam mixture were treated with 52.27 pounds of nitrogen per acre of fertilizer on a granular carrier (the same fertilizer product used in Example 7) and from 0 to 10 pounds per acre of maleic hydrazide in liquid form. A second series of plots were treated with the same rate of fertilizer and from 0 to 0.1875 pounds per acre of EL-500, also in liquid form. Maleic hydrazide presented no activity below a rate of about 1 pound per acre. Thus, it was necessary to use a 100/1 ratio of maleic hydrazide to EL-500 to afford any comparison. Based on leaf fresh weight, FIG. 6 compares the percent of retardation of the two treatments at various application rates of the growth regulators. It is apparent from FIG. 6 that maleic hydrazide, like AC 925, exhibits a virtual on/off switch mode of activity induced by mitotic inhibition as contrasted with the gradual retardation provided by the gibberellin retardant, EL-500. The maleic hydrazide shows a narrow range of biological activity, from about 1 or 1.5 pounds per acre to 4.7 pounds per acre, for inhibition levels from well over 70% all the way down to 10% of the control, fertilized without growth regulator.

In contrast, turf treated with a fertilizer plus EL-500 exhibits a more gradual slope. The range of activity for EL-500 is from a level of retardation of about 70% to 24% of the control over a much wider range of application rates. This graph points out the much greater range of safety involved with the use of the compositions of the invention.

EXAMPLE 11

Mitotic inhibitors are frequently phytotoxic to newly planted turf. The aforesaid U.S. Pat. No. 3,462,257 covers the use of combination fertilizer products containing 6 azauracil only on mature turf.

Figure 7:
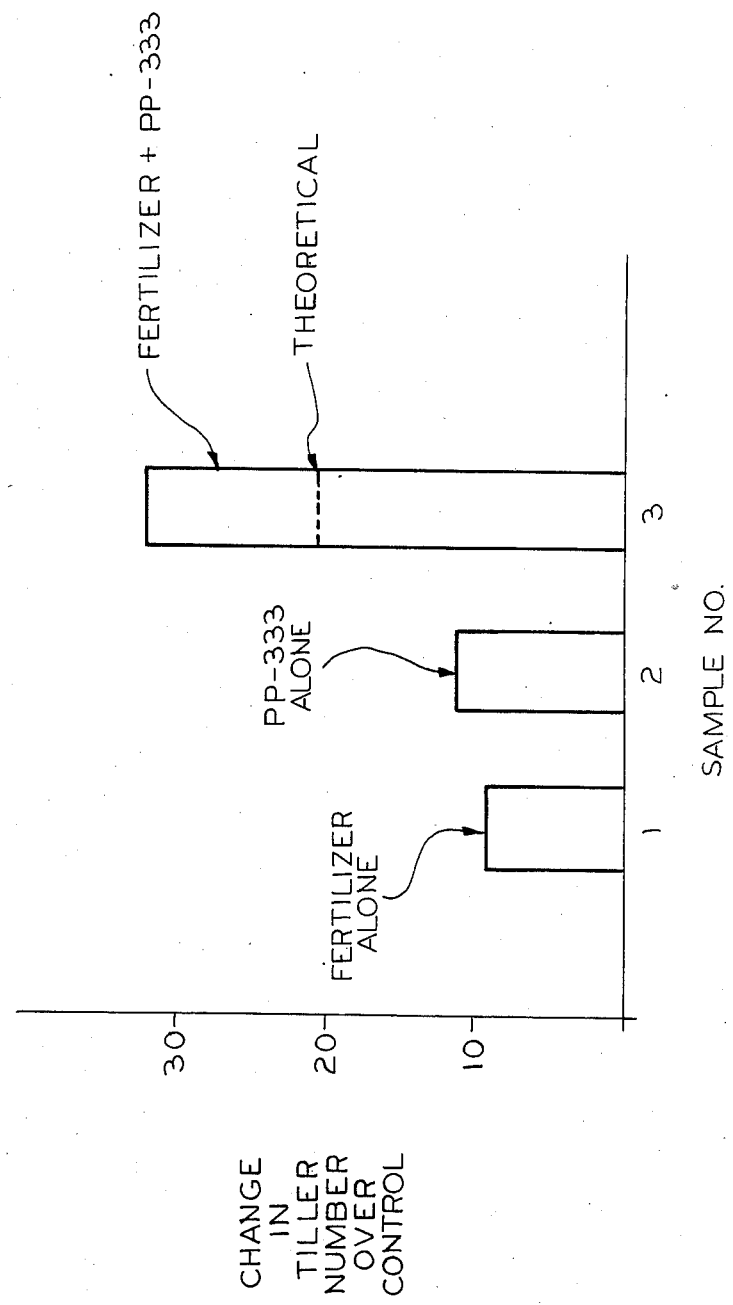
FIG. 7 is a bar graph showing the change in tiller number produced by the compositions of the invention on newly planted turf as compared to the same fertilizer or growth regulator alone.

Enhancing the establishment of newly seeded or sprigged turf is highly desirable (reduces erosion and increases the asthetic value of the area). In this example, fertilizer and PP-333 were applied to newly planted turf. Victa Kentucky bluegrass was seeded in 2" pots using 15 seeds per square inch. Five weeks after germination, on a silt loam soil, the plants were treated with fertilizer and PP-333 applied separately and in combination. The fertilizer was a high phosphorus fertilizer formulated on vermiculite as a carrier having a 18-24-6 analysis of N, $P_2O_5$ and $K_2O$ derived from urea, methylene ureas, monoammonium phosphate and potassium chloride with 47% of the nitrogen in slow release methylene urea form. FIG. 7 shows, in bar graph form, the change in tiller number per sample as compared to an untreated control. In sample 1, the fertilizer alone was applied at 40 pounds of nitrogen, 53 pounds of $P_2O_5$ and 13 pounds of $K_2O$ per acre. In sample 2, PP-333 was applied alone at 0.125 pounds per acre on a vermiculite carrier. In sample 3, both the fertilizer and the growth regulator were applied at the same rates as sample 1 and sample 2. The bar for sample 3 shows the actual as well as the theoretical response of the combination of fertilizer and PP-333. The theoretical response assumes the effect of the fertilizer and PP-333 were additive. As shown in FIG. 7, all formulations increased the tiller number over the control (zero on the vertical axis). However, when the fertilizer and growth regulator were applied simultaneously to the same plants, a synergistic response was realized as compared to their expected combined response. Note the actual response of the fertilizer plus PP-333 (bar 3) is substantially greater than the response which should have been theoretically obtained by combining fertilizer and PP-333.

EXAMPLE 12

A series of tests were made to measure surge growth, color, quality and density of turf treated with a fertilizer only product and turf treated with the same fertilizer in combination with PP-333. The combination product was prepared from the following formulation:

|  | % |
|---|---|
| Fertilizer[1] | 96.28 |
| Sticking Agent (Polyvis OSH)[2] | 2.56 |
| Attaclay dust | 0.76 |
| PP-333 50% | 0.40 (0.20) |

[1]The same fertilizer shown in Example 1.
[2]A polybutene sticking agent.

The PP-333, as a 50% wettable powder, was blended together with the attaclay dust. This mixture was fed dry into a blender containing the fertilizer base. The sticking agent was then sprayed onto this mixture with agitation in the ribbon blender.

A five year old stand of a blend of Victa, Bristol and Baron Kentucky bluegrass, grown in the field on Morley silty clay loam, was treated with the foregoing combination product and with the same product without the PP-333. The turf had been maintained at a 2" cutting height prior to treating. The turf exhibited good color at the initiation of the test. All materials were applied in granular form to dry foliage and watered in within 24 hours. A good irrigation program was followed to assure optimum growing conditions. The color, leaf fresh weight, quality and density were measured at intervals for 70 days. The results are set forth in Table VII.

TABLE VII

| Sample No | N lbs/A | PP-333 | Average[1] Color | Average[1] Quality | Total[1] Fresh. Wt. | Total[1] Density[2] |
|---|---|---|---|---|---|---|
| 1 | 26 | 0 | 8.0 | 2.8 | 1709 | 397 |
| 2 | 39 | 0 | 8.0 | 2.6 | 1884 | 383 |
| 3 | 26 | 0.20 | 9.6 | 1.4 | 1731 | 491 |

[1]Average or total of four measurements at 33, 44, 56 and 70 days.
[2]Based on fresh weight of clippings collected in a zone 2.5–3.0 inches above the soil.

As shown in Table VII, the sample 3 combination product enhanced both turf color and quality as compared to turf receiving either the same amount of fertilizer alone (sample 1) or 50% more fertilizer alone (sample 2). The total fresh weight for the turf treated with the combination product was intermediate between the two fertilized samples but density was substantially increased over both fertilized-only plots.

Figure 8:
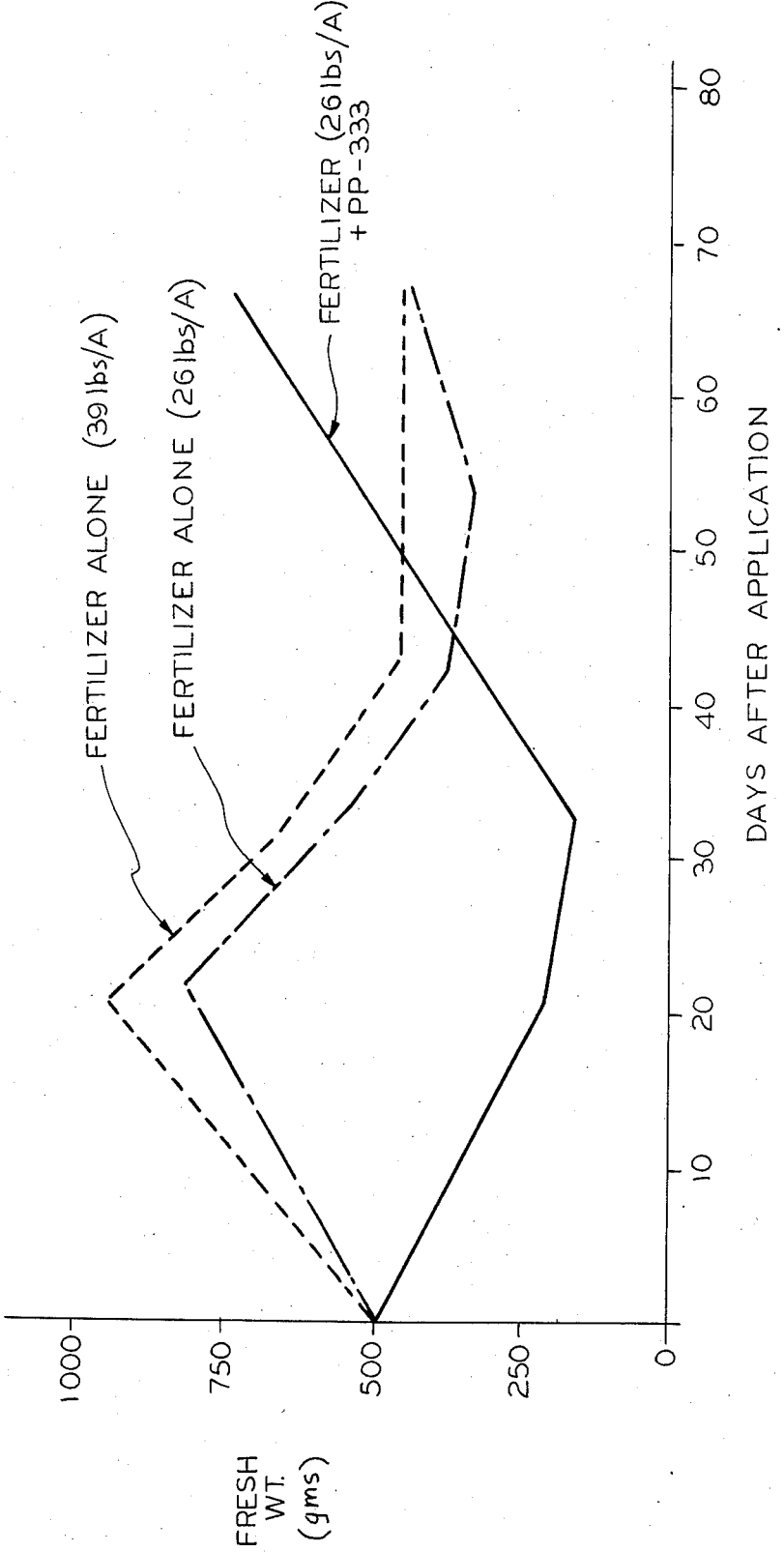
FIGS. 8 and 9 compare the combination products with various proportions of the fertilizer alone.

FIG. 8 illustrates the leaf fresh weight production over a 70 day test period as affected by fertilizer ±PP-333. As shown in this figure, surge growth was dramatically reduced (50–75%) for the first 33 days. Subsequent growth was principally due to increased density as shown by Table VII, which contributes to the esthetic value and the wear tolerance of the turf.

EXAMPLE 13

Turf treated with fertilizer and gibberellin synthesis retardants appear morphologically different than turf treated with fertilizer alone. In order to quantify these differences and determine if there were gross differences physiologically, turf treated with PP-333 was separated into various parts and analyzed. These tests were conducted as follows. Bristol Kentucky bluegrass was grown in a 3/1 sand/loam soil mixture fertilized with 43 pounds of nitrogen per acre on two different days, 33 days apart with the same 27-3-3 fertilizer only formulation used in Example 12. On the first day of fertilization, PP-333 was also applied to some of the turf samples using 10 ppm in 50 ml/0.08 square feet (0.6 pounds per acre). The plants were harvested five months (156 days) after the first treatment and the leaves, crown area (zero to 1 inch above soil level) thatch and roots were separated, dried, weighed and analyzed. Table VII shows the distribution of plant growth as affected by the presence or absence of PP-333 with the fertilizer.

TABLE VIII

| Plant Part | Fertilizer Without PP-333 gm | %[1] | Fertilizer With PP-333 gms | %[1] | % increase or decrease |
|---|---|---|---|---|---|
| Leaf | .41 | 12 | .37 | 10 | −10 |
| Crown | 1.54 | 45 | 2.14 | 58 | +39 |
| Thatch | .82 | 24 | .51 | 14 | −38 |
| Roots | .65 | 19 | .65 | 18 | 0 |
| Total Dry Wt. | 3.42 | 100 | 3.67 | 100 | |

[1]% of total weight of the plant

As shown by Table VIII, the total dry weight of the plants was not significantly altered by either treatment. However, there was a change in the distribution of the weight of the various parts of the plant. Turf treated with the combination products exhibited a 39% increase in crown weight and a 38% decrease in thatch weight. Leaf and root weights were not significantly altered. The increase in crown weight supports findings set forth in previous examples of improved density as contrasted with increased height. Thatch reduction is a substantial benefit since thatch build up often leads to injury of the turf. Thatch is partially decomposed plant material that collects between the crown of the grass plant and the soil surface.

Table IX shows the percent nutrient content of various plant parts from the foregoing tests, again as affected by the presence or absence of PP-333 with the fertilizer.

TABLE IX

| Nutrient % | Fertilizer ± PP-333 | | | | | | | | |
|---|---|---|---|---|---|---|---|---|---|
| | Leaf | | | Crown | | | Root | | |
| | (−) | (+) | % change | (−) | (+) | % change | (−) | (+) | % change |
| N | 1.84 | 3.56 | +93 | 1.06 | 2.30 | +116 | 0.92 | 1.02 | +11 |
| P | 0.26 | 0.42 | +62 | 0.22 | 0.32 | +45 | 0.13 | 0.16 | +23 |
| K | 1.62 | 2.23 | +38 | 0.80 | 1.75 | +119 | 0.21 | 0.15 | −29 |
| Average | | | +64 | | | +93 | | | +2 |

The nutrient content was increased from 38–93% in the leaves and from 45–119% in the crown in the plants which were treated with the fertilizer product containing PP-333. There was little change in the roots. This increase in nutrient content, particularly nitrogen in the leaf (93%), explains the enhanced color following treatment with the combination fertilizer product.

EXAMPLE 14

An additional series of tests were run to determine whether the nitrogen removed in the leaf tissue is altered by the presence of a gibberellin synthesis retardant in the fertilizer product. A Victa/Bristol/Baron Kentucky bluegrass mixture grown under field conditions was treated with the same granular fertilizer formulation shown in Example 12 plus and minus various concentrations of PP-333. Forty four days after treatment, leaf tissue was collected from the plots, weighed, dried and analyzed for nitrogen content. The results are set forth in Table X.

TABLE X

| Sample No | N lbs/A | PP-333 | Dry Wt (gm/1000 sq ft) | N[1] |
|---|---|---|---|---|
| 1 | 26 | 0 | 1448 | 51 |
| 2 | 39 | 0 | 1695 | 63 |
| 3 | 26 | 0.30 | 838 | 33 |

[1]Nitrogen weight in the dry tissue.

As shown in Table X the amount of nitrogen obtained from the clippings (33 gms/1000 sq. ft.) treated with the combination product was substantially less than that obtained from the turf treated with either the same amount (sample 1) or 50% more (sample 2) fertilizer without the PP-333. These data indicate that a substantial proportion of the nitrogen was conserved by not being removed in the clippings when treated with the combination product. The data thus shows less total nitrogen uptake and thus an improvement in nutrient residual achieved when using a fertilizer product plus a gibberellin synthesis retardant as compared to the same fertilizer alone.

EXAMPLE 15

Additional tests were conducted to determine if lower rates of nitrogen in combination with PP-333 would provide turf performance comparable to higher rates of nitrogen in the absence of PP-333 (increasing nitrogen efficiency). Bristol Kentucky bluegrass was grown in silica sand and was maintained on a complete Hoagland solution varying in nitrogen content. Half of the plots were treated with PP-333 using the equivalent of 0.018 pounds per acre in a liquid drench. The modified Hoagland solution was applied weekly at 25, 50, 100 and 200 ppm nitrogen, which is equal to 5.44, 10.89, 21.28 and 43.56 pounds of nitrogen per acre per month. At various periods after treatment, leaf color and plant quality were recorded. The response of the turf at the conclusion of 49 days is set forth in Table XI.

TABLE XI

| Sample No | N (ppm) | Leaf Color (10 > 1) Without PP-333 | Leaf Color (10 > 1) With PP-333 | Plant Quality (1 > 10) Without PP-333 | Plant Quality (1 > 10) With PP-333 |
|---|---|---|---|---|---|
| 1 | 25 | 4.0 | 7.0 | 5.0 | 3.0 |
| 2 | 50 | 5.0 | 7.0 | 5.0 | 2.7 |
| 3 | 100 | 6.0 | 9.0 | 4.0 | 1.0 |
| 4 | 200 | 7.0 | 10.0 | 3.0 | 1.0 |

Table XI shows that the color and quality of turf treated with the combination product was as good as or better than the corresponding color and quality of turf treated with four times the nitrogen level without PP-333. For example, sample 2 (50 ppm N) shows a color level of 7 and a quality level of 2.7 for 50 ppm of N with PP-333 added. The same color level and an essentially comparable quality level was achieved in sample 4 but required 200 ppm of N when the fertilizer was used alone. These data support the increased nitrogen efficiency when using the composition of this invention.

EXAMPLE 16

Figure 9:
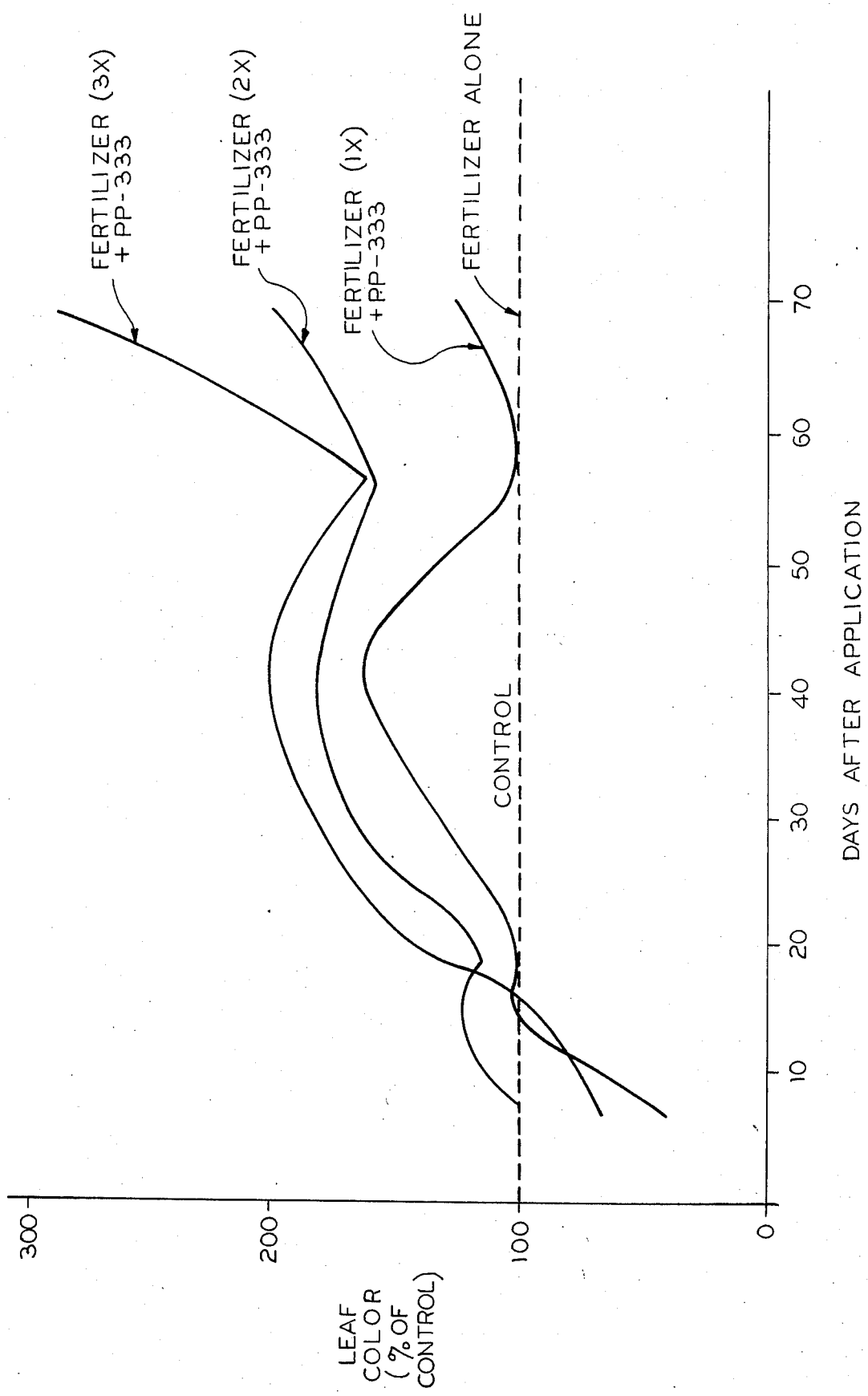

One of the advantages of the use of combination fertilizer products containing a gibberellin synthesis retardant is the enhancement of fertilizer response following the slowed growth phase. This is demonstrated by the following tests. Bristol Kentucky bluegrass was grown in 4 inch pots containing a 3/1 sand/loam soil mixture. The turf was treated with fertilizer alone at the rate of 21.78 pounds per acre of nitrogen and with one, two and three times that fertilizer rate alone and combined with 0.06 pounds of PP-333 per acre. The fertilizer formulation was again that used in Example 12. Each was applied at the same time but separately as a dry (fertilizer) or liquid (PP-333) formulation. The leaf color results are shown in FIG. 9 in which the color levels are shown as a percent of the control which received fertilizer alone. It can be seen from FIG. 9 that at the same fertilizer rate, the color at day 70 with the combination product was 25% better than the corresponding fertilizer control. When the fertilizer rate was doubled, the color was 200% better than the control and 300% better when the rate was tripled, relative to respective fertilizer controls. This improvement is an order of magnitude higher than the color improvement for comparable rates of combination products containing 6 azauracil as shown in the aforesaid U.S. Pat. No. 3,462,257.

EXAMPLE 17

An additional series of tests were conducted to compare the effect of the presence of the gibberellin synthesis retardant when the plants emerge from the slowed growth phase. Bristol Kentucky bluegrass was grown in 4 inch pots containing a 3/1 sand/loam soil mixture and treated with granular formulations of fertilizer (the formulations shown in Examples 1 and 2) with and without PP-333. Rates of 58.8 pounds of nitrogen and 0.18 pounds of PP-333 per acre were evaluated. The residual characteristics of the fertilizer as enhanced by the addition or PP-333 is shown in Table XII.

TABLE XII

| Treatment | N (lbs/A) | PP-333 (lbs/A) | Day of Observation 55 | 66 | 88 |
|---|---|---|---|---|---|
| A. Color (10 > 1) | | | | | |
| Control (No fert) | 0 | 0 | 1.0 | 1.0 | 1.0 |
| Fert. only | 58.8 | 0 | 2.0 | 3.7 | 3.0 |
| Fert + PP-333 | 58.8 | 0.18 | 5.0 | 10.0 | 10.0 |
| B. Quality (1 > 10) | | | | | |
| Control (No fert) | 0 | 0 | 10.0 | 9.0 | 7.7 |
| Fert. only | 58.8 | 0 | 8.0 | 6.7 | 6.0 |
| Fert. + PP-333 | 58.8 | 0.18 | 5.3 | 1.0 | 2.0 |
| C. Height (cms) | | | | | |
| Control | 0 | 0 | 0.83 | 1.00 | 1.50 |
| Fert. only | 58.8 | 0 | 1.67 | 1.67 | 2.20 |
| Fert. + PP-333 | 58.8 | 0.18 | 1.00 | 1.83 | 2.50 |
| D. Fresh Weight (gms) | | | | | |
| Control | 0 | 0 | — | 0.15 | 0.19 |
| Fert. only | 58.8 | 0 | — | 0.61 | 0.43 |
| Fert. + PP-333 | 58.8 | 0.18 | — | 0.64 | 0.86 |

Note the dramatic improvement in turf color and quality with fertilizer containing PP-333 as compared to fertilizer only treated turf. At the end of 88 days, the color of the turf treated with fertilizer + PP-333 was 10 compared to 3 for the turf treated with fertilizer alone. The improvement occurred without a reduction in growth rate after the 66th day of the test, based on height and fresh weight. The combination fertilizer products produced slightly taller turf than the fertilized only samples at the end of 88 days but the fresh weight yields were twice those of the fertilized only turf. Thus, the densities for the turf treated with the combination product were considerably greater.

EXAMPLE 18

In this example, turf quality and fresh weight were compared at various intervals over a 129 day period for a series of turf samples treated with fertilizer and two different rates of the PP-333 growth regulator. Bristol Kentucky Bluegrass was treated with the granular fertilizer formulation of Example 12 while the PP-333 was added as a liquid drench using the equivalent of 0.25 inches of water (50 ml/0.07925 sq ft). Turf quality and fresh weight were recorded periodically. In order to maintain turf color and quality, fertilizer was reapplied at the same 32.7 pounds of nitrogen per acre rate to sample 2 (fertilizer only) on the 56th day of the test. The results are set forth in Table XIII.

TABLE XIII

| Sample No | N[1] lbs/A | PP-333 lbs/A | Total F.W. Gms[2] | %[3] | Quality[4] Day 56 | Day 129 | Average[5] |
|---|---|---|---|---|---|---|---|
| 1 | 0 | 0 | 1.24 | 22 | 5.0 | 4.0 | 4.6 |
| 2 | 32.7(× 2) | 0 | 5.57 | 100 | 3.7 | 2.7 | 2.6 |
| 3 | 32.7 | 0.06 | 3.71 | 67 | 3.3 | 3.0 | 3.1 |
| 4 | 32.7 | 0.30 | 2.23 | 40 | 3.3 | 1.7 | 2.8 |

[1]Sample 2 was refertilized on 56th day.
[2]Total Fresh Wt gms. is the sum of fresh wt cuttings at six intervals.
[3]Based on % of the fertilizer standard (sample 2).
[4]Turf Quality: 1–3 is excellent; 4–6 is fair.
[5]Average of quality readings at six intervals.

The reapplication of fertilizer in the middle of the 129 day test resulted in a surge of growth for sample 2. Although not shown in the table, the surge growth was a 100 to 400% increase over the combination products containing PP-333. Since the turf treated with the fertilizer PP-333 combination product (samples 3 and 4) continued to exhibit good quality, no repeat treatment was needed. Thus, a treatment program of fertilizer plus growth regulator provides quality turf for a period of up to 120 days while repeat applications of fertilizer alone are needed every 60 days to produce the same quality levels. Moreover, the fertilizer growth regulator program resulted in more uniform turf growth with less total growth (fresh wt of sample 4 is 40% of sample 2) and no loss of turf quality as compared to a fertilizer program alone.

EXAMPLE 19

A series of tests were carried out to compare the biological activity and nutrient efficiency of the combination fertilizer products of the invention on turf grown on different soil types. Bristol Kentucky bluegrass was grown in 6 soil types collected from 5 different states. The turf was grown in quart containers under greenhouse conditions. The plots were treated with from 0 to 0.48 pounds per acre of PP-333. All plots were fertilized with 52.27 pounds N/acre with the same fertilizer used in Example 18 at the same time the PP-333 was applied. Retardation, as a percent of the control, was measured by leaf fresh weight over a seven week period. The results are set forth in Table XIV.

TABLE XIV

| PP-333 Sample | lbs/acre | Soil Location Retardation as Percent of Control Ohio | MD | Calif | Fla. | Texas | Av. |
|---|---|---|---|---|---|---|---|
| 1 | 0 (Control) | 100 | 100 | 100 | 100 | 100 | 100 |
| 2 | 0.06 | 85 | 67 | 72 | 59 | 63 | 69 |
| 3 | 0.12 | 74 | 55 | 51 | 35 | 46 | 54 |
| 4 | 0.24 | 53 | 30 | 22 | 22 | 23 | 32 |
| 5 | 0.48 | 37 | 22 | 23 | 15 | 19 | 23 |

As shown in Table XIV, fresh weight of the turf was reduced after seven weeks irrespective of soil type as a result of combination fertilizer PP-333 treatment.

EXAMPLE 20

The tests of Example 19 with fertilizer products and PP-333 were extended on the six soil types to 85 days. In addition, the tests were also carried out with a fertilizer product and EL-500 as the growth regulator. On the 85th day, a number of observations were recorded. Tests were carried out at the same rates for both PP-333 and EL-500. in all but samples 2 and 6. The results set forth in Table XV are the average of the six soils tested.

TABLE XV

| | lbs/A | | FW (gms) | | Ht. (cm) | | Ht/FW | | Quality (1 > 10) | | Color (10 > 1) | |
|---|---|---|---|---|---|---|---|---|---|---|---|---|
| Sample | N | PGR | PP 333 | EL 500 | PP 333 | EL 500 | PP 333 | EL 500 | PP 333 | EL 500 | PP 333 | EL 500 |
| 1 | 1.2 | 0 | .35 | .35 | 3.2 | 3.2 | 9.1 | 9.1 | 6.2 | 6.2 | 3.7 | 3.7 |
| 2 | 1.2 | .05 | .47 | — | 3.0 | — | 6.3 | — | 5.1 | — | 5.0 | — |
| 3 | 1.2 | .10 | .60 | .48 | 3.2 | 3.1 | 5.3 | 6.5 | 4.1 | 4.9 | 6.6 | 6.1 |
| 4 | 1.2 | .20 | .63 | .55 | 3.0 | 3.0 | 4.8 | 5.5 | 2.6 | 3.6 | 8.5 | 7.4 |
| 5 | 1.2 | .40 | .43 | .49 | 2.3 | 2.5 | 5.3 | 5.1 | 2.4 | 2.5 | 9.8 | 9.6 |
| 6 | 1.2 | .80 | — | .25 | — | 1.6 | — | 6.4 | — | 3.0 | — | 10.3 |
| 7 | 0 | 0 | .22 | .22 | 2.7 | 2.7 | 12.2 | — | 6.6 | 6.6 | 3.3 | 3.3 |

Table XV shows that the fresh weight increases with increasing rate of growth regulator up to 0.40 pounds per acre. However, this increase was not associated with a corresponding increase in plant height, indicating that turf density was increased, a result reflected in the Ht/FW ratios (lower ratios indicating shorter, denser turf). Note also that turf quality and color increased with increasing rates of the growth regulator. The color for sample 6 of 10.3 at 0.80 pounds per acre of EL-500 reflects an unnatural green color resulting from too high a rate of growth regulator. Table XV thus shows an increased nutrient efficiency on a variety of soil types for combination fertilizer products containing both EL-500 and PP-333 growth regulator.

EXAMPLE 21

This example was carried out to determine the biological response of a variety of fertilizers in the presence of PP-333, the various fertilizers having different water solubility. Bristol Kentucky bluegrass grown on a 3/1 sand/loam mixture was fertilized with various liquid nitrogen sources using 65.3 pounds of N per acre contained in 348.5 gallons of water. The solutions containing either fertilizer alone or fertilizer and 0.058 pounds per acre (20 ppm) of PP-333 was applied as a foliar spray and watered in after 28 hours. The turf was evaluated periodically for leaf fresh weight production and turf quality over a 24 day period. The fertilizers used in these tests were the following:

Fluf (trademark)—flowable urea formaldehyde in the form of a water suspension of methylene urea with 70% of the nitrogen in a slow release form (methylene urea) having an analysis of 18-0-0.

Formolene (trademark)—a water solution of urea and methylene urea with 50% of the nitrogen as urea with an analysis of 30-0-2. The potassium is derived from potassium formate and potassium bicarbonate.

Urea—a granular high analysis nitrogen source (46-0-0), considered a fast release nitrogen fertilizer.

The results of the foregoing tests are set forth in Table XVI.

TABLE XVI

| Sample No | N Source | PP-333 lbs/A | Total[1] Fr. Wt. (%) | Quality (1 > 10) Day 24 |
|---|---|---|---|---|
| 1 | Fluf | 0.058 | 71 | 2.0 |
| 2 | Formolene | 0.058 | 45 | 1.0 |
| 3 | Urea | 0.058 | 42 | 1.0 |
| 4 | None | 0.058 | 103 | 7.0 |
| 5 | Fluf | 0 | 100 | 2.0 |
| 6 | Formolene | 0 | 100 | 2.0 |
| 7 | Urea | 0 | 100 | 2.0 |
| 8 | Control | 0 | 100 | 8.0 |

[1]As a percent of samples 5-8.

As shown in Table XVI, fresh weight production was decreased and quality was increased in most cases when fertilizer was used in the presence of PP-333 regardless of nitrogen source. Although quality was the same in samples 1 and 5, the quality was maintained in sample 1 with 29% less growth.

EXAMPLE 22

In this example, tests were conducted with additional nitrogen sources to compare the biological response with and without the addition of a gibberellin synthesis retardant. The nitrogen sources were methylene urea (40% N, 36% cold water insoluble nitrogen-CWIN), ureaform (38% N, 75% CWIN), isobutylidene diurea (IBDU-31% N, 90% CWIN), oxamide (31% N, 73% CWIN) and urea (46% N, 0% CWIN). Ureaform is a slow release nitrogen source made by the condensation of urea and formaldehyde. IBDU is a slow release nitrogen source made by the condensation of urea and isobutyraldehyde. Oxamide is a slow release nitrogen source made by reacting cyanogen with concentrated hydrocloric acid. Fresh weights were recorded periodically to obtain surge growth during the first 4 weeks and residual response during the remainder of the 70 day test. The reduction in surge growth of turf treated with the combination products of the invention as compared with the corresponding growth of turf treated with the same amount of fertilizer alone is set forth in Table XVII. The percentages were obtained by weighing the fresh weight of turf harvested on the 14th and 28th day after initiation of the tests. All plots were treated with 65.34 pounds of nitrogen and 0.06 pounds of PP-333 per acre.

TABLE XVII

| Nitrogen Source | Reduction in Surge Growth (%)[1] |
|---|---|
| Methylene Urea | 86 |
| Ureaform | 75 |
| IBDU | 80 |
| Oxamide | 72 |
| Urea | 80 |

[1]Percent reduction relative to turf treated with the various nitrogen sources alone.

Surge growth was thus reduced irrespective of nitrogen source. However, surge growth was more dramatically reduced when methylene urea was the nitrogen source.

EXAMPLE 23

Tests were conducted with a sulfur coated urea fertilizer to determine the biological response of this slow release fertilizer type both with and without a growth regulator. The sulfur coated urea was a slow release encapsulated urea granule prepared by spraying preheated urea granules with molten sulfur. The resulting product had 37% N, 30% S, with 53% of the nitrogen releasing from the granules in 1 week. Bristol Kentucky bluegrass was grown in 4 inch cups containing a 3/1 sand/loam soil mixture. The encapsulated fertilizer and liquid PP-333 were applied simultaneously to dry turf using various rates of nitrogen in combination with either zero or 0.6 pounds per acre of PP-333. Sixteen weeks after treatment, the quality of the turf was recorded and is set forth in Table XVIII.

TABLE XVIII

| Sample No | Fertilizer Nitrogen lbs/acre | Turf Quality (1 > 10) lbs/acre of PP-333 | |
|---|---|---|---|
| | | 0 | 0.6 |
| 1 | 0 | 5.0 | 4.7 |
| 2 | 21.7 | 4.7 | 2.0 |
| 3 | 54.4 | 4.3 | 2.3 |
| 4 | 135.0 | 4.0 | 1.3 |

The quality of the turf was improved in the presence of both the fertilizer and PP-333 regardless of nitrogen rate.

EXAMPLE 24

Tests were conducted to determine the response of combination products containing gibberellin synthesis retardants to warm season grasses grown in the Apopka, Fla. area under field conditions. The turf was grown in a Leon fine sandy loam soil. Granular formulations of fertilizer and plant growth regulators were applied to Tifway bermudagrass to determine tolerance and response limits. The fertilizer formulations were the same as those in Example 12. The EL-500 formulations were 92.9% corncob carrier, 6.18% methyl carbitol solvent and 0.9% EL-500. The EL-500 was dissolved in the solvent and sprayed onto the corncob carrier in a blender. In a first series of tests from 0.5 to 1.5 pounds per acre of EL-500 in combination with the fertilizer were applied to bermudagrass and compared to turf receiving fertilizer alone. The results after 62 days are shown in Table XIX.

TABLE XIX

| Sample No. | N lbs/acre | lbs/acre EL-500 | Observations | |
|---|---|---|---|---|
| | | | Color 10 > 1 | Injury % |
| 1 | 65.34 | 0.5 | 8.3 | 0 |
| 2 | 130.68 | 1.0 | 7.3 | 15 |
| 3 | 196.00 | 1.5 | 6.3 | 20 |
| 4 | 65.34 | — | 8.3 | 0 |
| 5 | 130.68 | — | 9.0 | 0 |
| 6 | 190.00 | — | 9.7 | 0 |

It is apparent that amounts of the growth regulator of 1.0 or more injured the bermudagrass as compared to the same amounts of fertilizer alone.

EXAMPLE 25

Figure 10:
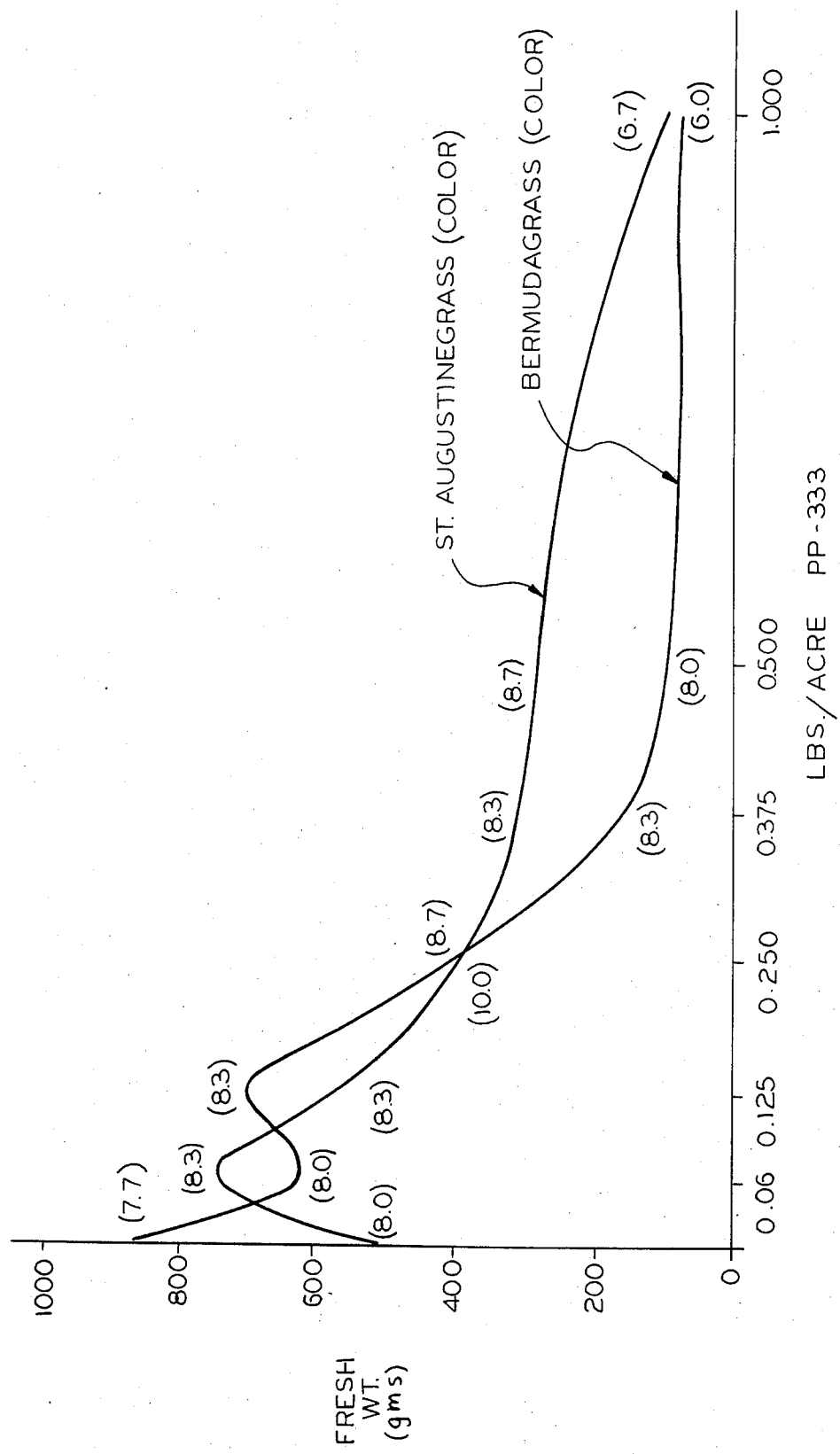
FIGS. 10 and 11 are similar comparative graphs showing the results of the invention with southern grasses.
Figure 11:
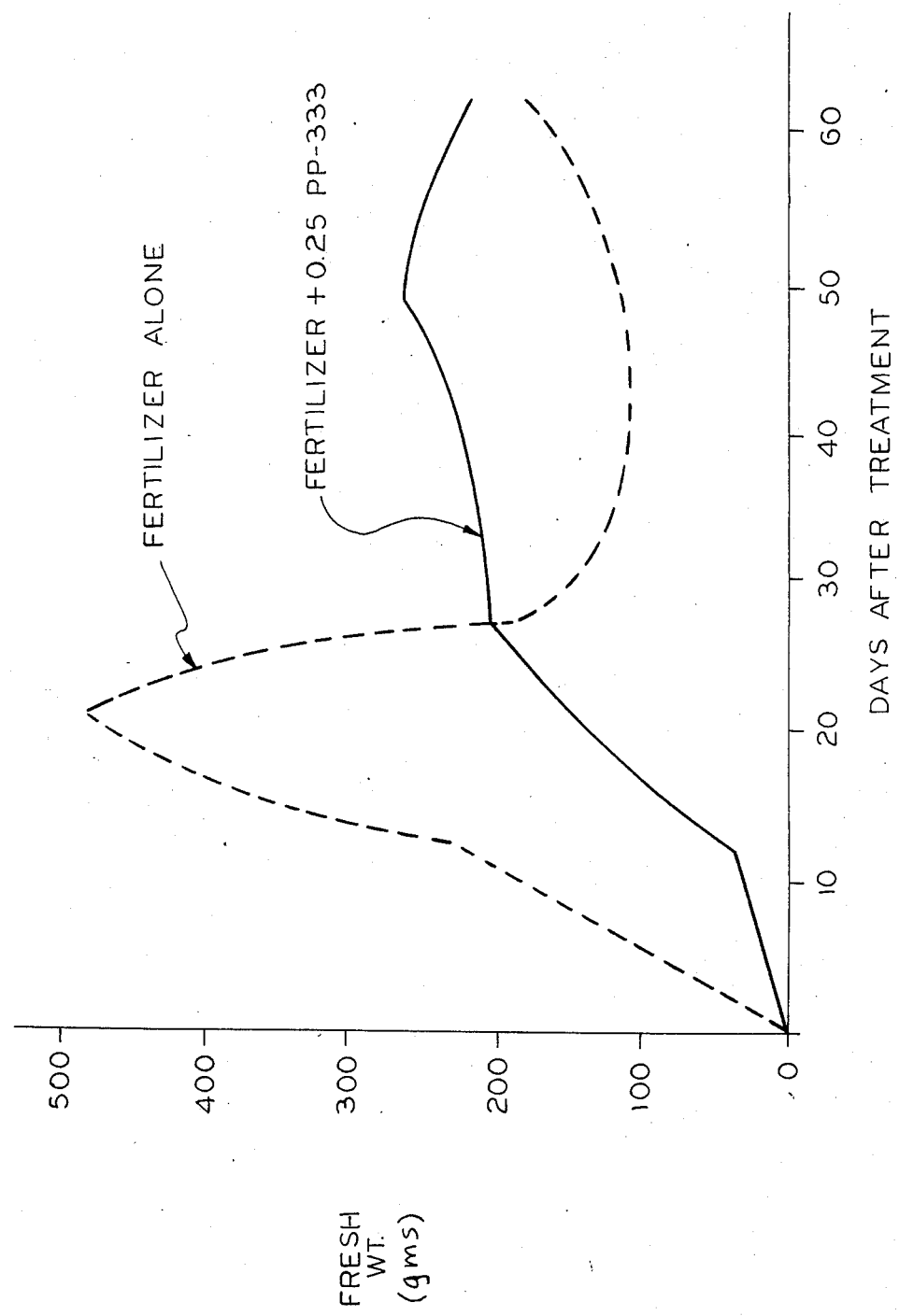

An additional series of tests were conducted as in Example 24 but with lower rates of the growth regulator with both bermudagrass and St. Augustinegrass and these results are shown in FIG. 10. Using from zero to 0.50 pounds per acre of PP-333 and fertilizer caused a substantial reduction of cumulative leaf fresh weight during a 28 day test period without a reduction in turf color (shown in parentheses along the curves). A higher rate of 1 pound per acre caused a reduction in turf color. The data are charted over a 63 day time period in FIG. 11 for bermudagrass. It is clear from FIG. 11 that an initial surge of growth, based on leaf fresh weight, with fertilizer alone was eliminated when the fertilizer was combined with PP-333 at 0.25 pounds per acre. Note the substantially more uniform growth pattern following treatment with the combination product containing 0.25 pounds per acre of PP-333. These data indicate that southern grasses respond to gibberellin retardants much like northern grasses. Other studies of Bitterblue and Floratam St. Augustinegrass showed response very similar to bermudagrass when treated with fertilizer products in combination with PP-333 and EL-500.

EXAMPLE 26

In this example, the gibberellin synthesis retardant in the combination fertilizer product of the invention was combined with very low rates of mefluidide, a mitotic inhibitor; and the results were compared with the fertilizer alone (of Example 12) and with the fertilizer in combination with each growth regulator alone. Bristol Kentucky bluegrass was grown in a 3/1 sand/loam mixture and fertilized with 52.27 pounds per acre of nitrogen. Mefluidide was applied at 0.05 pounds per acre as a foliar spray using 8 gallon per 1000 square feet while PP-333 was applied at 0.06 pounds per acre as a drench (50 ml/0.07925 square feet). The height 36 days after application is shown in Table XX.

TABLE XX

| Sample | lbs/acre | | | |
|---|---|---|---|---|
| No | N | PP-333 | Mefluidide | Height* |
| 1 | 52.27 | 0 | 0 | 100 |
| 2 | 52.27 | 0 | 0.05 | 96 |
| 3 | 52.27 | 0.06 | 0 | 71 |
| 4 | 52.27 | 0.06 | 0.05 | 7 |

*% of Control, nitrogen only (sample 1).

This table shows a dramatic reduction in height with the fertilizer plus both growth regulators and only a slight to moderate reduction with each regulator alone. The reduction with PP-333 alone was substantial even though a very small amount was used.

EXAMPLE 27

Additional tests were conducted to compare combination fertilizer products containing PP-333 with and without mefluidide. In these tests, even lower rates of mefluidide were combined with lower rates of PP-333 on a granular urea-formaldehyde fertilizer carrier. Mefluidide is disclosed in the literature for use in liquid form as a spray at from 0.25 to as high as 1 pound per acre. These tests show the effect with mefluidide with a granular formulation.

The fertilizer and combination fertilizer—PP-333 formulations were those of Example 12. The formulation containing mefluidide was as follows:

| | Percent |
|---|---|
| Fertilizer | 93.54 |
| Polyvis OSH | 3.08 |
| Methyl Carbitol | 1.14 |

-continued

| | Percent |
|---|---|
| T-Det N-95 | 0.37 |
| Hi Sil 233 | 1.47 |
| PP-333 (50%) | 0.38 (0.19) |
| Mefluidide (90%) | 0.02 (0.018) |

The 90% technical grade mefluidide was dissolved in a mixture of methyl carbitol and the T-Det N-9.5 solution. This solution was sprayed onto the Hi Sil dust. The dust was blended with the PP-333 wettable powder and fed into a blender containing the fertilizer carrier (the fertilizer was the same as that of Example 12). The Polyvis OSH sticking agent was sprayed onto the fertilizer/dust mixture to adhere the active dust to the fertilizer particle.

The products were applied to Victa/Bristol/Baron Kentucky bluegrass and the results measured at the middle and end of a 96 day test period. Results for color and quality are shown in Table XXI.

TABLE XXI

| Sample | lbs/acre | | | Color (10 > 1) | | Quality (1 > 10) | |
|---|---|---|---|---|---|---|---|
| | | | Me- | Day after application | | | |
| No | N | PP-333 | fluidide | 43 | 96 | 43 | 96 |
| 1 | 26.1 | 0 | 0 | 8.0 | 6.0 | 3.0 | 4.0 |
| 2 | 26.1 | 0.2 | 0 | 8.7 | 9.3 | 1.7 | 1.0 |
| 3 | 26.1 | 0.2 | 0.02 | 9.3 | 9.5 | 1.3 | 1.3 |
| 4 | 39.2 | 0 | 0 | 10.0 | 7.0 | 1.3 | 3.0 |

Table XXI shows that color and quality improvement trends were evident on the 43rd day and that on the 96th day color and quality were superior with turf treated with the combination fertilizer product containing either PP-333 or PP-333 and mefluidide as compared to turf fertilized with the same amount of fertilizer alone (sample 1) or with 50% more fertilizer alone (sample 4). With 0.02 pounds per acre of mefluidide in combination with 0.2 pounds per acre of PP-333, the color and quality were enhanced even more than PP-333 alone.

EXAMPLE 28

The following results show fresh weight measurements of leaf tissue at various intervals over a 70 day period for the same treatment set forth in the previous example. For turf density measurements, turf was cut at 3 inches and the clippings collected following a second mowing at 2.5 inches. Density in Table XXII is as a percent of the control (Sample 1).

TABLE XXII

| Sample | lbs/acre | | | Fresh Wt. (gms/42 sq. ft.) | | | | Density |
|---|---|---|---|---|---|---|---|---|
| | | | Me- | Day of Observation | | | | % |
| No | N | PP-333 | fluidide | 16 | 29 | 43 | 61 | 70 |
| 1 | 26.1 | 0 | 0 | 245 | 293 | 277 | 175 | 100 |
| 2 | 26.1 | 0.2 | 0 | 172 | 208 | 455 | 446 | 260 |
| 3 | 26.1 | 0.2 | 0.02 | 126 | 146 | 407 | 412 | 250 |
| 4 | 39.2 | 0 | 0 | 343 | 417 | 412 | 268 | 146 |

It will be noted from Table XXII that the addition of mefluidide to the fertilizer product containing PP-333 resulted in a significant reduction in fresh weight up to 61 days following application as compared to fertilizer+PP-333 alone. The increase in fresh weight over the plants receiving fertilizer only (samples 1 and 4) was a result of increased turf density.

EXAMPLE 29

Table XXIII shows the effect of adding mefluidide to the combination fertilizer—PP-333 product on the nitrogen removed in the leaf clippings after the 16th day of the tests. The tests were again carried out as set forth in Example 27.

TABLE XXIII

| Sample No | lbs/acre N | PP-333 | Mefluidide | Nitrogen removal gms/1000 sq. ft. |
|---|---|---|---|---|
| 1 | 26.1 | 0 | 0 | 51.3 |
| 2 | 26.1 | 0.2 | 0.2 | 23.9 |
| 3 | 39.2 | 0 | 0 | 70.0 |

Table XXIII shows that the addition of both PP-333 and mefluidide can drop the nitrogen removal rate by as much as ½ to ⅔ as compared to a plot which is only fertilized—compare sample 2 with samples 1 and 3. The reduction in nitrogen removal was accompanied by an improvement in quality level (see Table XXI). This again demonstrates that the nutrient demand is dramatically reduced with the combination products, particularly in the presence of mefluidide, as compared to the fertilizer alone.

EXAMPLE 30

Example 27 was again repeated but on tall fescue instead of Kentucky bluegrass. The tests were carried out with 0.5 pounds per acre of PP-333 and either zero or 0.05 pounds per acre of mefluidide. The results of these tests are set forth in Table XXIV at the end of 56 days.

TABLE XXIV

| Sample No | lbs/acre N | PP-333 | Mefluidide | Color (10 > 1) | Quality (1 > 10) |
|---|---|---|---|---|---|
| 1 | 32.7 | 0 | 0 | 6.7 | 3.3 |
| 2 | 32.7 | 0.5 | 0 | 7.3 | 3.0 |
| 3 | 32.7 | 0.5 | 0.05 | 9.0 | 1.0 |
| 4 | 39.2 | 0 | 0 | 6.0 | 3.7 |

Table XXIV shows that tall fescue responds similarly to Kentucky bluegrass. The color and quality of the combination product was improved by the addition of mefluidide. In all cases, the combination products (with PP-333 alone or PP-333 and mefluidide) induced a superior turf response (color and quality) as compared to the fertilized only plots.

EXAMPLE 31

A wide variety of turfgrasses representing cool and warm season grasses were treated with a wide range of N/PGR ratios using nitrogen sources containing a minimum of 50% water soluble nitrogen. The optimum N/PGR ranges for turf performance for these grasses are set forth in Table XXV.

TABLE XXV

| Turf Type | N/PGR |
|---|---|
| Bentgrass | 130–544 |
| Bluegrass | |
| Fine Fescuegrass | |
| Tall Fescuegrass | 64–130 |
| Ryegrass | |
| Common Bermudagrass | 47–256 |
| Hybrid Bermudagrass | 40–256 |
| St Augustinegrass | 65–256 |

As shown in Table XXV, the optimum N/PGR ratio for fine leaf cool season grasses (bentgrass, bluegrass and fine fescuegrass) ranges from 130–544. For coarse leaf cool season grasses (tall fescuegrass and ryegrass), a lower range is more desirable (64–130). Warm season grasses (bermudagrass and St. Augustinegrass) exhibit optimum performance when the N/PGR ratio ranges from 40–256.

EXAMPLE 32

Figure 12:
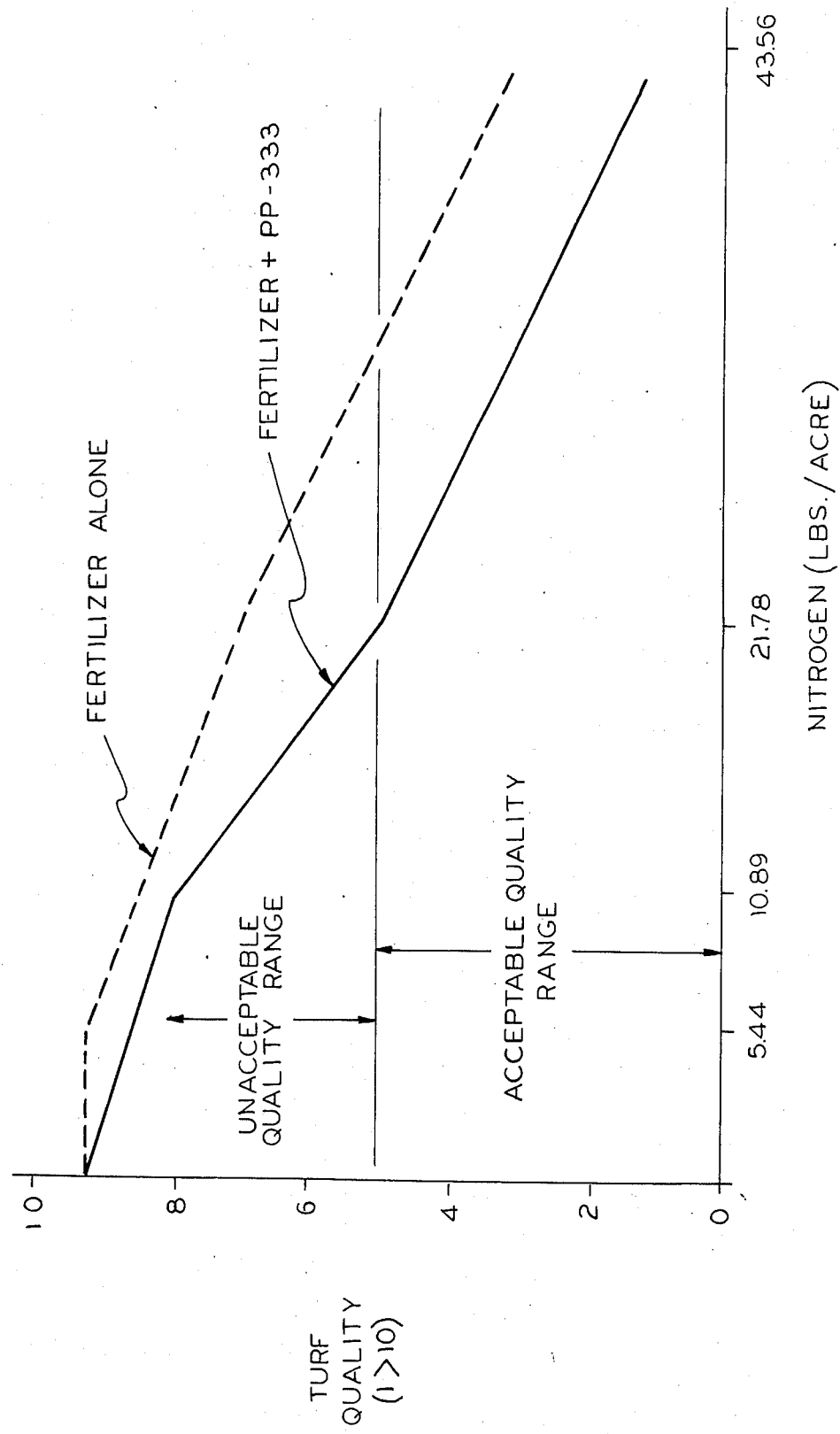
FIGS. 12 and 13 are additional graphs comparing the fertilizer alone with the combination products.

Bristol Kentucky bluegrass was grown in 4″ pots containing sand and maintained with a complete Hoagland solution varying in nitrogen content. Half of the plots were treated with the equivalent of 0.06 pounds of PP-333 per acre. As shown in FIG. 12, at low rates of nitrogen (5.44–10.89 pounds per acre), the addition of PP-333 had basically no effect on turf quality. At higher rates of nitrogen (21.70–43.5 pounds per acre), PP-333 improved turf quality as compared to the control.

Figure 13:
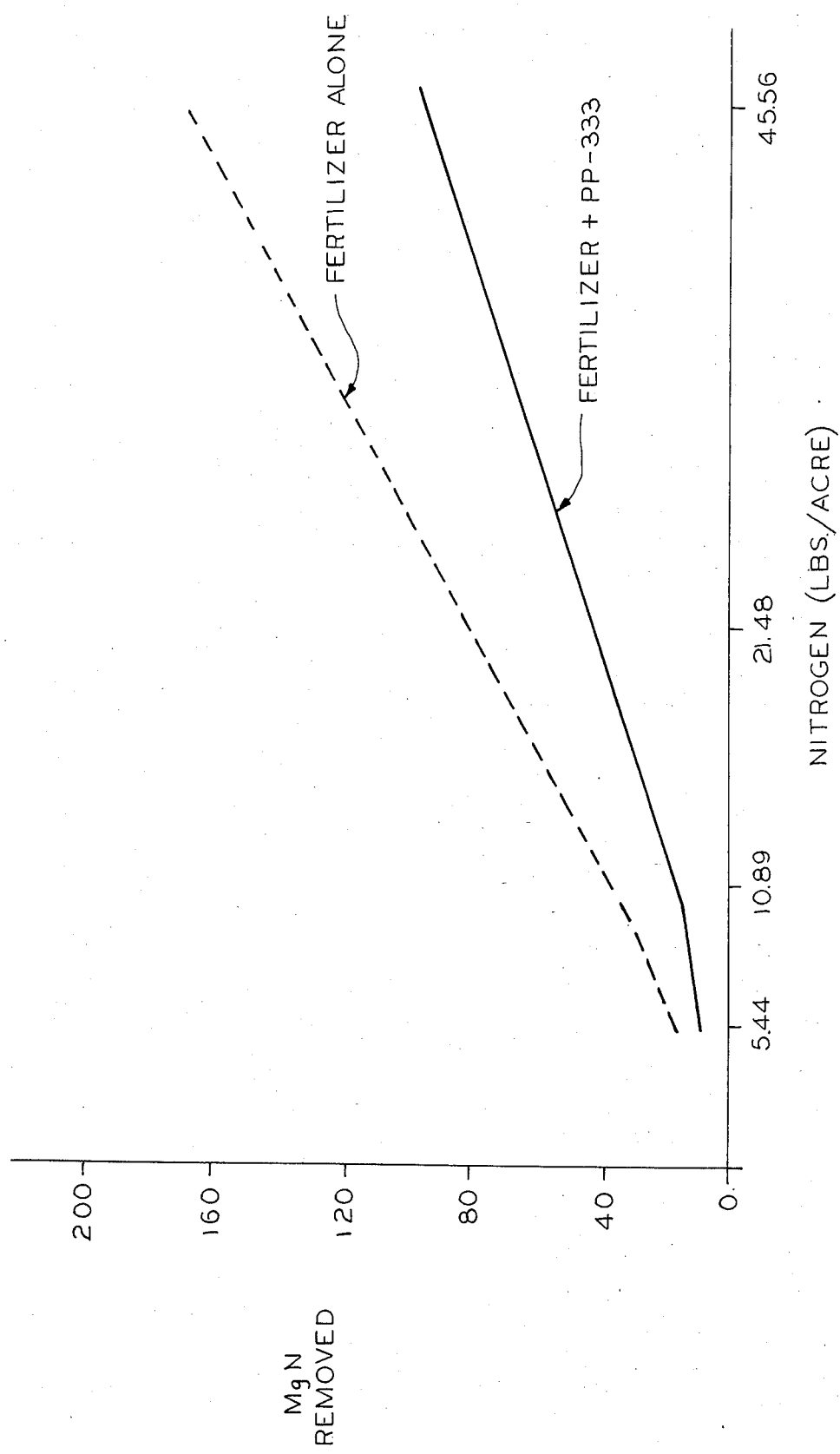

This interaction was also apparent when nitrogen removed in the clippings was studied. As shown in FIG. 13, the milligrams of nitrogen removed in the tissue treated with PP-333 was decreased over the control at all rates of nitrogen. However, there was very little effect at the low nitrogen level, below about 10.89 pounds per acre. At the higher nitrogen levels, there is a dramatic reduction in nitrogen removed when PP-333 is added.

EXAMPLE 33

Figure 14:
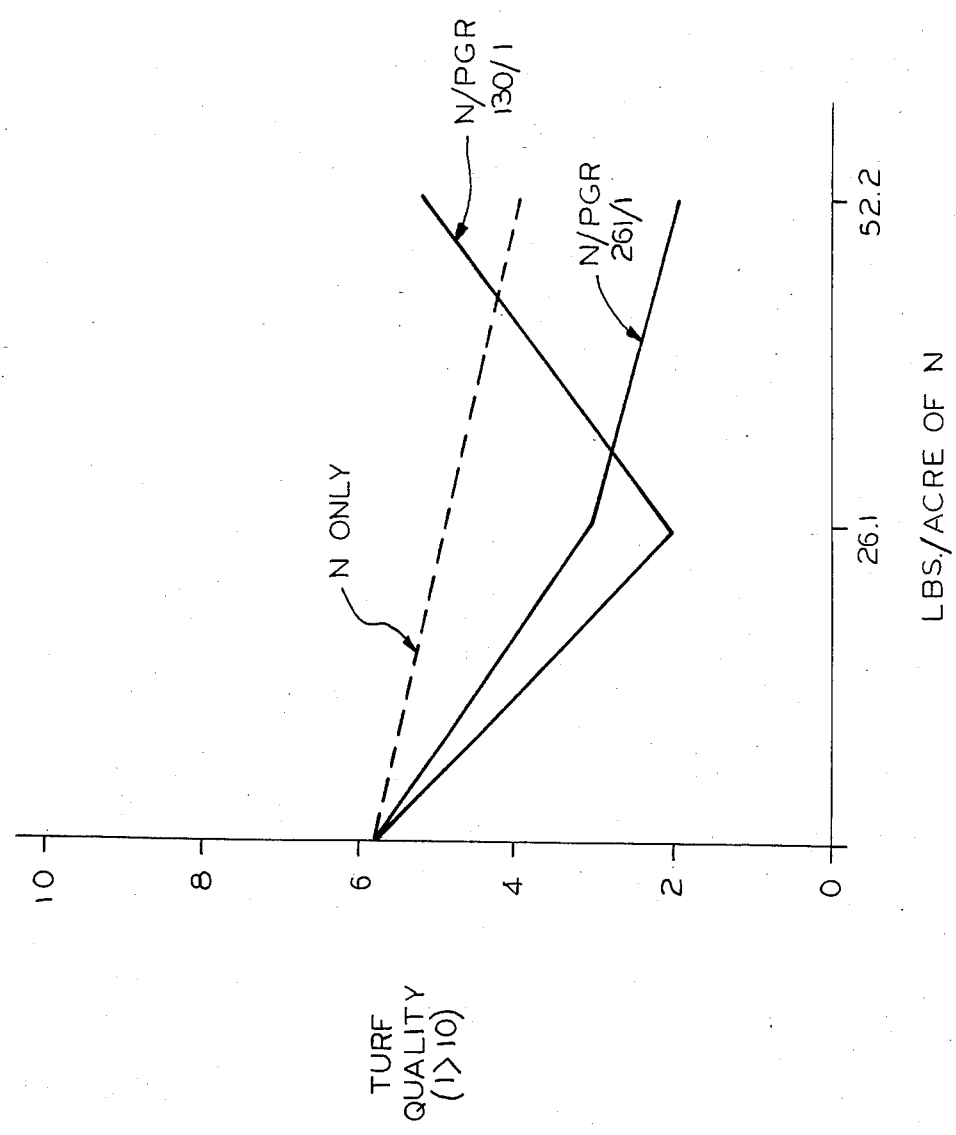
FIGS. 14 and 15 are graphs illustrating the importance of the ratio of nitrogen to plant growth regulator.

A granular urea-formaldehyde fertilizer was applied at 26.1 pounds of nitrogen per acre to Victa/Bristol/Baron Kentucky bluegrass alone or in combination with PP-333 at 0.1 or 0.2 pounds per acre using a single (26.1 pounds per acre) rate of nitrogen and at 0.2 or 0.4 pounds per acre of PP-333 with a double (52.2 pounds per acre) rate of nitrogen. The N/PGR ratio was maintained at 261/1 with the lower PGR rate and at 130/1 with the higher PGR rate. Materials were applied to dry turf and watered in. Test results are shown in FIG. 14 on the 35th day after initial application. As shown in FIG. 14, the quality of turf improved with increasing rate of product when treated with fertilizer alone and dramatically improved with fertilizer plus the lower (0.1 or 0.2) rate of PP-333 at a N/PGR ratio of 261/1. In contrast, with increasing rate of product, plots treated with fertilizer plus the higher rate of PP-333 deteriorated in quality. This observation again illustrates the significance of the N/PGR ratio and rate for obtaining quality turf.

EXAMPLE 34

Figure 15:
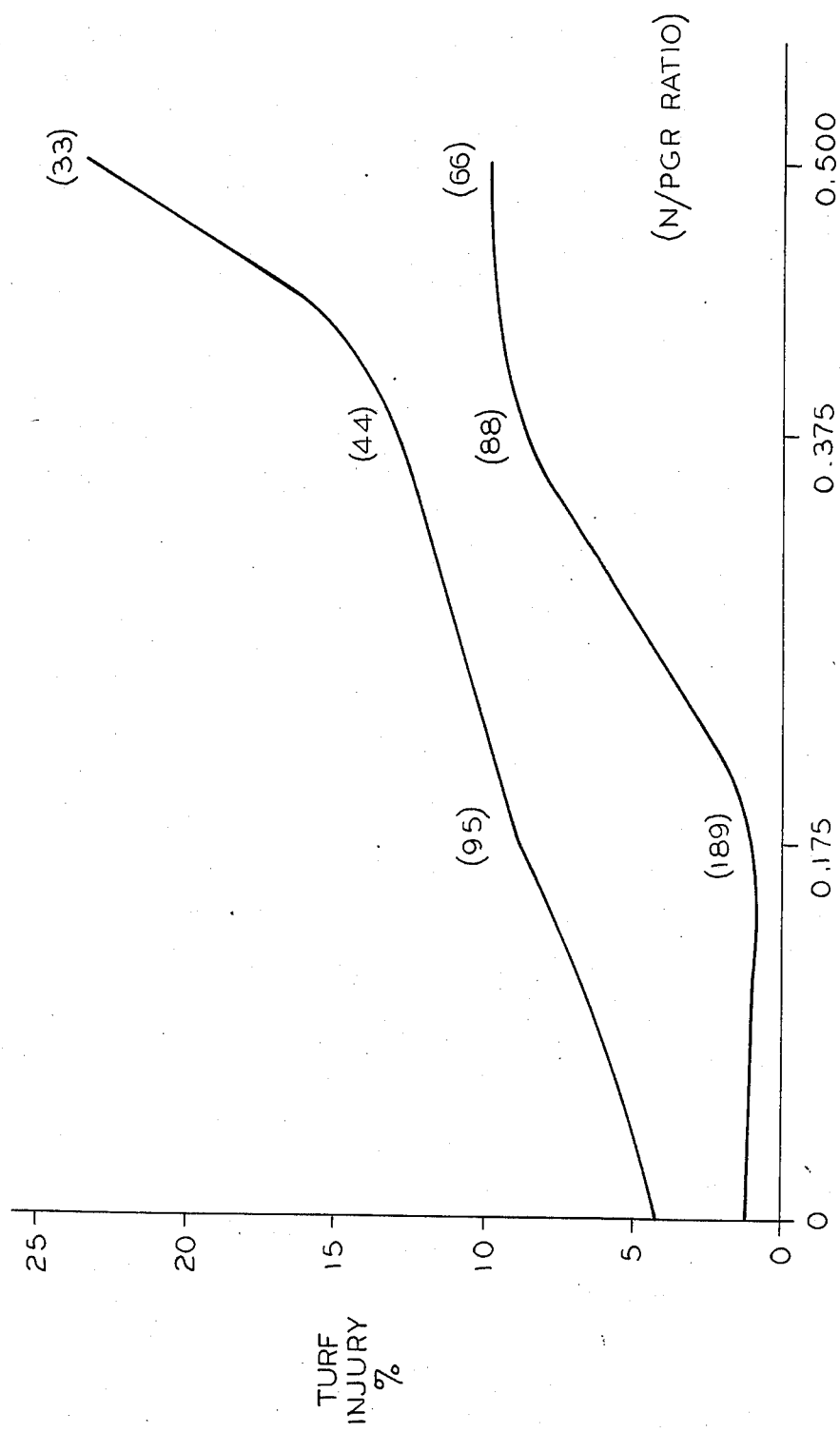

Kentucky bluegrass (Victa, Bristol, Vantage) sod was treated with granular fertilizer formulations containing various N/PGR ratios. The nitrogen was applied at 16.6 or 33.1 pounds per acre in combination with 0, 0.175, 0.375, or 0.50 pounds PP-333 per acre. As shown in FIG. 15, ratios of N/PGR ranging from 66 to 95 caused approximately 10% injury to bluegrass. Lower ratios (44 and 33) caused more injury with the latter very objectionable. Higher ratios (189) dramatically reduced the injury (1% injury). This again illustrates the significance of the N/PGR ratios.

The invention as previously indicated is particularly useful for the treatment of turf, including cool season grasses such as Poa spp (bluegrasses), Lolium spp (ryegrasses), Fustuca spp (fescuegrasses) and Agrostis spp (bentgrasses); and warm season grasses such as Stenotaphrum spp (St. Augustinegrasses), Cynodon spp (bermudagrasses) and Paspalum spp (bahiagrasses). As indicated throughout the specification, the precise ranges of fertilizer and growth regulator, as well as the precise ratios of nitrogen to plant growth regulator, vary depending upon the type of turf treated, the type of fertilizer used and its mode of application. However, these ranges will all fall within the general ranges of overall proportions and amounts set forth in the claims which follow. The fertilizer may be any nitrogen fertilizer of the type use on turf, including both fast and slow release granular and liquid formulations. Examples of useful slow release granular nitrogen fertilizer formulations are set forth in U.S. Pat. Nos. 3,705,794 to Czurak et al, 4,025,329 to Goertz and 4,378,238 to Goertz. As set forth in these patents, the fertilizers may be accompanied by nutrients and micronutrients in addition to nitrogen and by other active ingredients, the latter including herbicides, fungicides and other pesticides.

We claim:

1. A composition for treating turf comprising
a nitrogen containing fertilizer and from 0.006 to 0.60 pounds of a plant growth regulator selected from the group consisting of paclobutrazol and flurprimidol, said amount being based on an amount of the composition for treating one acre of turf, said plant growth regulator being a compound which regulates the growth of vegetation by retardation of gibberellin synthesis,
the ratio by weight of nitrogen in said fertilizer to said plant growth regulator being at least forty to one,
said fertilizer and plant growth regulator being present in said composition in a proportion which is effective when applied to turf to improve the quality of the turf, the improvement in quality being both greater and extending for a longer period than that resulting from the application of the fertilizer or plant growth regulator alone.

2. The composition of claim 1 in which the plant growth regulator is paclobutrazol.

3. The composition of claim 1 in which the plant growth regulator is flurprimidol.

4. The composition of claim 1 in which the composition is a granular formulation.

5. The composition of claim 1 in which the composition is a liquid formulation.

6. The composition of claim 1 in which the fertilizer is a fast release fertilizer.

7. The composition of claim 6 in which the fast release fertilizer is urea.

8. The composition of claim 1 in which the fertilizer is a slow release fertilizer.

9. The composition of claim 8 in which the fertilizer is sulfur coated urea.

10. The composition of claim 8 in which the fertilizer is methylene urea.

11. The composition of claim 1 in which the plant growth regulator is present in an amount of 0.05 to 0.5 pounds, based on an amount for treating one acre of vegetation.

12. A composition for treating turf comprising a nitrogen containing slow release fertilizer containing from 20 to 180 pounds of nitrogen and from 0.006 to 0.60 pounds of a plant growth regulator selected from the group consisting of paclobutrazol and flurprimidol, said amount being based on an amount of the composition for treating one acre of turf,
the ratio by weight of the nitrogen in said fertilizer to said plant growth regulator being at least forty to one,
said fertilizer and plant growth regulator being present in said composition in proportions which is effective when applied to turf to improve the quality of the vegetation, the improvement in quality being both greater and extending for a longer period than that resulting from the application of the fertilizer or plant growth regulator alone.

13. A process for treating turf comprising
applying to the turf a nitrogen containing fertilizer and from 0.006 to 0.60 pounds per acre of a plant growth regulator selected from the group consisting of paclobutrazol and flurprimidol, said plant growth regulator being a compound which regulates the growth of vegetation by retardation of gibberellin synthesis,
the ratio by weight of nitrogen in said fertilizer to said plant growth regulator being at least forty to one,
said fertilizer and plant growth regulator being applied in proportions which are effective to improve the quality of the turf, the improvement in quality being both greater and extending for a longer period than that resulting from the application of the fertilizer or plant growth regulator alone.

14. The process of claim 13 in which the plant growth regulator is paclobutrazol.

15. The process of claim 13 in which the plant growth regulator is flurprimidol.

16. The process of claim 13 in which the turf is cool season grass.

17. The process of claim 16 in which the ratio by weight of nitrogen to said plant growth regulator is from 60 to 600 to one.

18. The process of claim 13 in which the turf is a warm season grass.

19. The process of claim 18 in which the ratio by weight of nitrogen to said plant growth regulator is from 40 to 300 to one.

20. The process of claim 13 in which the fertilizer and plant growth regulator are applied to the turf as a granular composition in a single application.

21. The process of claim 13 in which the fertilizer and plant growth regulator are applied to the turf as a liquid composition in a single application.

22. The process of claim 13 in which the fertilizer is a fast release fertilizer.

23. The process of claim 22 in which the fast release fertilizer is urea.

24. The process of claim 13 in which the fertilizer is a slow release fertilizer.

25. The process of claim 24 in which the fertilizer is sulfur coated urea.

26. The process of claim 24 in which the fertilizer is methylene urea.

27. The process of claim 13 in which the fertilizer is applied in an amount of from 20 to 180 pounds of nitrogen per acre.

28. The process of claim 13 in which the growth regulator is applied in an amount of from 0.05 to 0.5 pounds per acre.

29. A process for treating turf comprising
applying to the turf a nitrogen containing slow release fertilizer containing from 20 to 180 pounds of nitrogen per acre in combination with from 0.006 to 0.60 pounds per acre of a plant growth regulator selected from the group consisting of paclobutrazol and flurprimidol, the ratio by weight of nitrogen in the fertilizer to said plant growth regulator being at least forty to one, the fertilizer and plant growth regulator being applied in proportions which is effective to improve the quality of the turf, the improvement in quality being both greater and extending for a longer period than that resulting from the application of the fertilizer or plant growth regulator alone.

30. The process of claim 13 in which the fertilizer and plant growth regulator are applied separately, the plant growth regulator being applied while the turf is actively growing as a result of the application of the fertilizer.

31. The process of claim 13 in which the fertilizer and plant growth regulator are applied separately, the fertilizer being applied before damage to the turf by the plant growth regulator.

* * * * *